United States Patent
Oh et al.

(10) Patent No.: US 8,318,856 B2
(45) Date of Patent: Nov. 27, 2012

(54) NUCLEIC ACID DELIVERY SYSTEM COMPRISING CONJUGATES OF PEI AND HYALURONIC ACID

(75) Inventors: Yu-Kyoung Oh, Seoul (KR); Hyun-Gu Kang, Pohang (KR); Ji-Seok Kim, Pohang (KR); Jiang Ge, Pohang (KR); Ki-Su Kim, Pohang (KR); Ki-Tae Park, Jeongju (KR); Su-Eun Han, Yongin (KR); Ga-Yong Shim, Yongin (KR); Ii-Hwan Cho, Ansan (KR); Sei-Kwang Hahn, Pohang (KR)

(73) Assignees: Postech Academy-Industry Foundation, Pohang (KR); Korea University Industry and Academy Collaboration Foundation, Seoul (KR)

( * ) Notice: Subject to any disclaimer, the term of this patent is extended or adjusted under 35 U.S.C. 154(b) by 313 days.

(21) Appl. No.: 12/733,061

(22) PCT Filed: Apr. 4, 2008

(86) PCT No.: PCT/KR2008/001914
§ 371 (c)(1),
(2), (4) Date: Feb. 4, 2010

(87) PCT Pub. No.: WO2009/020270
PCT Pub. Date: Feb. 12, 2009

(65) Prior Publication Data
US 2010/0144035 A1     Jun. 10, 2010

(30) Foreign Application Priority Data
Aug. 9, 2007 (KR) .................. 10-2007-0080276

(51) Int. Cl.
C08B 37/00     (2006.01)
C08G 63/48     (2006.01)
C08G 63/91     (2006.01)
A61K 48/00     (2006.01)

(52) U.S. Cl. .................. 525/54.3; 514/44 R

(58) Field of Classification Search .......... None
See application file for complete search history.

(56) References Cited

U.S. PATENT DOCUMENTS
5,591,140 A * 1/1997 Narayanan et al. ........... 604/269

FOREIGN PATENT DOCUMENTS
JP    2005-176830    7/2005

OTHER PUBLICATIONS

Han, et al. (2009) "Cationic derivatives of biocompatible hyaluronic acids for delivery of siRNA and antisense oligonucleotides" Journal of Drug Targeting, 17(2): 123-32.*
Ito Tomoko et al. 'Hyaluronic acid and its derivative as a multifunctional gene expression enhancer: protection from non-specific interactions, adhesion to targeted cells, and transcriptional activation.' J Control Release. vol. 112(3) pp. 382-388, May 30, 2006.
Stephanie Werth et al. 'A low molecular weight fraction of polyethylenimine (PEI) displays increased transfection efficiency of DNA and siRNA in fresh or lyophilized complexes' J Control Release. vol. 112(2) pp. 257-270, May 15, 2006.
Godbey et al.,Poly(ethylenimine) and its role in gene delivery, J. Controlled Release 60 (1999)149-160.
M.A.Gosselin M.A. et al., Efficient Gene Transfer Using Reversibly Cross=Linked Low Molecular Weight Polyethylenimine, Bioconjugate Chem. 12 (2001) 989-994.
Erbacher P. et al., Transfection and Physical Properties of Various Saccharide, Polu(ethylene glycol), and Antibody-Derivatized Polyethylenimines (PEI), J. Gene. Med. 1 (1999) 210-222.

* cited by examiner

*Primary Examiner* — Robert M Kelly
(74) *Attorney, Agent, or Firm* — Lexyoume IP Meister, PLLC.

(57) ABSTRACT

The present invention relates to a delivery system for nucleic acid using a cationic polymer conjugate, and more specifically relates to a delivery system for nucleic acid comprising a cationic polymer conjugate prepared by conjugating hyaluronic acid or its derivative and polyethyleneimine, and a composition of delivering a nucleic acid into mammalian cell comprising a complex of the nucleic acid and a cationic polymer conjugate with electrostatic binding.

8 Claims, 25 Drawing Sheets a b

US 8,318,856 B2

NUCLEIC ACID DELIVERY SYSTEM COMPRISING CONJUGATES OF PEI AND HYALURONIC ACID

CROSS REFERENCE TO RELATED APPLICATION

The present application claims priority to and the benefit of Korean patent application No. 2007-0080276 filed in the Korea Intellectual Property Office on Aug. 9, 2007, the entire content of which is incorporated hereinto by reference.

BACKGROUND OF THE INVENTION (a) Field of the Invention

The present invention relates to a delivery system of nucleic acid comprising a cationic polymer conjugate prepared from hyaluronic acid or its derivative and polyethyleneimine, and more specifically, a composition for delivering a nucleic acid into mammalian cell comprising a complex of a cationic polymer conjugate prepared from hyaluronic acid or its derivative and polyethyleneimine, and nucleic acid bound to the cationic polymer conjugate through an electrostatic interaction.

(b) Description of the Related Art siRNA, antisense oligonucleic acids, plasmid deoxyribonucleic acid, and etc. are recently very important in the medicinal industrial fields as a nucleic acid drug. To develop the nucleic acid as a medicine, the most important problem is efficient delivery of the nucleic acid into cell or tissue. To deliver the nucleic acid into cell, viral vector or non-viral vectors, such as a polymer and nanoparticle, have been researched. The viral vector is advantageous in higher efficiency of the gene delivery than non-viral vector. However, the viral vector has a problem of safety in use, and thus has very limiting range for being used for human.

Non-viral vector has been developed as an alternative for viral vector. Cationic polymer, polyethyleneimine (PEI) forms colloidal particle with nucleic acid having negative charge, and has a pH buffering capacity in lysosome. Thus, it has been reported that PEI transfers plasmid deoxyribonucleic acid into various cells [Godbey et al., J. Controlled Release 60 (1999) 149-160]. However, there are many researches to solve the problems of the gene transfer efficiency into cell and cytotoxicity. Gosselin et al. reported that crosslinked PEI having low molecular was used for gene transfer [M. A. Gosselin M. A. et al., Bioconjugate Chem. 12 (2001) 989-994]. The PEI having low molecular weight shows low cytotoxicity, but lower gene expression efficiency than PEI 25K.

To reduce the cytotoxicity of PEI, PEI has been modified with dextran sulfate, human serum albumin, polyethylene glycol and etc., but all modified PEI show lower gene delivery efficiency than unmodified PEI. According to Erbacher et al., when a complex of nucleotide and the modified PEI with polyethylene glycol is administered to in vivo, spatial stability effect of "brush" layer, caused by the polyethylene glycol part on complex surface, increases circulation time of nucleotide in blood flow, but also lower delivering efficiency than unmodified PEI [Erbacher P. et al., J. Gene. Med. 1 (1999) 210-222].

Accordingly, the technology being capable of efficiently delivering oligonucleic acids such as siRNA and an antisense oligonucleic acid with low cytotoxicity needs in the field.

SUMMARY OF THE INVENTION

When an oligonucleic acid includes 200 base pairs or less, it shows lower negative charge than that of plasmid DNA. The efficiency of system of delivering plasmid DNA into cell cannot be applied for delivering oligonucleic acid. The present inventors developed that in order to efficiently deliver the oligonucleic acid having 200 base pairs or less such as siRNA and antisense oligonucleic acid, the conjugate of cationic polymer (PEI) and hyaluronic acid increases the delivering efficiency of the oligonucleic acids such as siRNA and antisense oligonucleic acid in various cell lines, and also reduces the cytotoxicity notably.

As the present inventors do every efforts to solve the unresolved problems of the prior art, they found that when the conjugate of hyaluronic acid or its derivative and PEI is used as a delivery system for a nucleic acid into mammalian cell, the cationic polymer conjugate increases the delivery efficiency of the nucleic acid of interest into the mammalian cell with low cytotoxicity.

Accordingly, the object of present invention is to provide a cationic polymer conjugate of hyaluronic acid or its derivative and PEI with high efficiency of delivering nucleic acid of interest into mammalian cell with the low cytotoxicity, and a composition for delivering the nucleic acid into a mammalian cell using this conjugate.

The other object of the present invention is to provide a method of delivering a nucleic acid into a mammalian cell by using the cationic polymer conjugate including hyaluronic acid or its derivative and PEI.

According to the embodiment of the present invention, because the method of delivering a nucleic acid by using the cationic polymer conjugate increases the delivery efficiency of the nucleic acid of interest into the mammalian cell with low cytotoxicity, it can be used for the technical field of delivering the oligonucleic acid.

BRIEF DESCRIPTION OF THE DRAWINGS

For more complete understanding of the present invention, and the advantages thereof, reference is now made to the following descriptions taken in conjunction with the accompanying drawings, in which.

DETAILED DESCRIPTION OF THE PREFERRED EMBODIMENTS

Figure 1A:
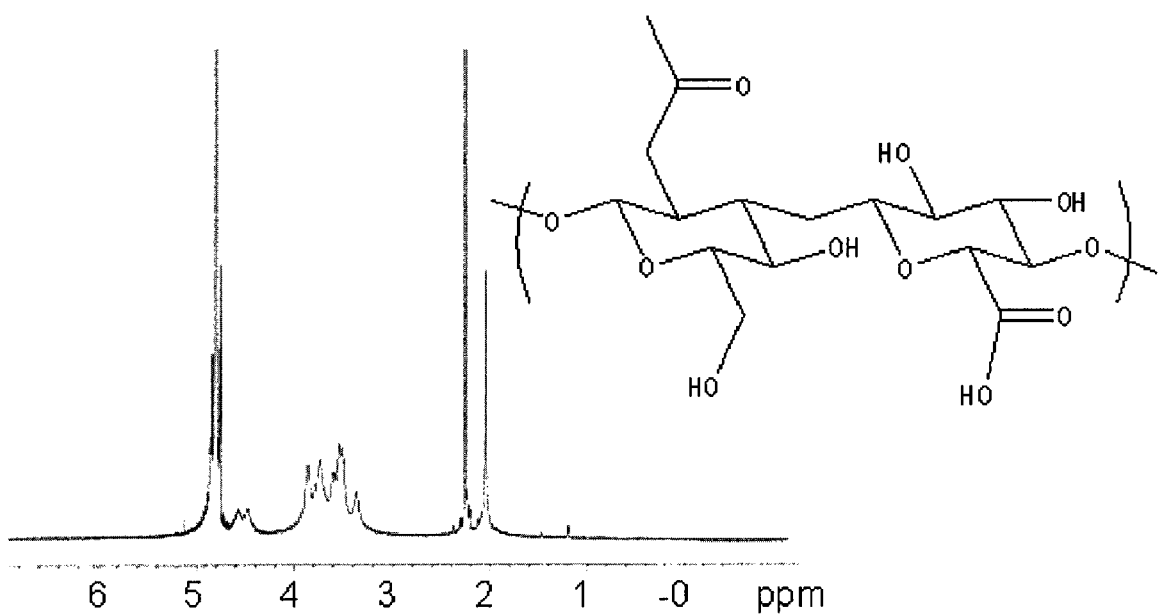
FIG. 1A to 1C are $^1$H nuclear magnetic resonance (NMR) result of (A) hyaluronic acid (HA) before conjugation, (B) PEI before conjugation, and (C) HA-PEI prepared in Example 32.

These and other objects of the invention will be more fully understood from the following description of the invention, the referenced drawings attached hereto and the claims appended hereto.

According to an embodiment of the present invention, a composition for delivering the nucleic acids into mammalian cell comprising cationic polymer conjugate prepared by conjugation (formation of chemical bond) of hyaluronic acid or its derivative and PEI.

Specifically, the present invention provides a cationic polymer conjugate prepared by conjugation of hyaluronic acid or its derivative and PEI, or a conjugate obtained by reacting hyaluronic acid and a compound having two or more carboxylic groups and then conjugating the hyaluronic acid derivative and PEI. The hyaluronic acid derivative is more preferably provided, because it increases the introduction rate of PEI with minimum chemical modification. The compound having two or more carboxyl groups, for examples, includes glutamic acid, gamma-carboxyl glutamic acid, aspartic acid, and glutathione, etc. but not limited thereto.

The composition of the present invention increases the delivery efficiency of various nucleic acids of interest such as siRNA, an antisense nucleic acid and the like into the mammalian cell by using cationic polymer conjugate as a carrier. The cationic polymer conjugate can form a complex with the nucleic acids by only mixing because of the electrostatic interaction between the positive charge of cationic polymer conjugate and the negative charge of nucleic acid.

In the composition for delivering the nucleic acid into mammalian cell, the hyaluronic acid has a molecular weight of 0.5 to 1,000 kD, and more preferably 10 to 900 kD.

In the composition, the PEI has a molecular weight of 0.8 to 250 kD and more preferably 1 to 80 kD.

In the composition, the mixing ratio of hyaluronic acid or its derivative and PEI contained in the cationic polymer conjugate can be not limited, as long as the cationic polymer conjugate can form a complex sufficiently by binding to the nucleic acid. Preferably, on the basis of 100 wt % of hyaluronic acid or its derivative and PEI, the amount of hyaluronic acid or its derivative is 1.5-50 wt % and the amount of PEI 50-98.5 wt %.

The crosslinking agent for the conjugation includes N-(2-dimethyl aminopropyl)-N'-ethylcarbodidimide) (EDC), 1-cyclohexyl-3-(2-morpholinoethyl) carbodiimide (CMC), dicyclohexyl carbodiimide (DCC), diisopropyl carbodiimide (DIC), N-ethyl-3-phenylisoxazolium-3'-sulfonate (Woodward's reagent K), N,N'-carbonyldiimidazole (CDI) and the like. Preferably, the conjugation may be performed by forming amide bond by conjugating —COOH group of hyaluronic acid and —NH$_2$ of polyethyleneimine using EDC, or carbamate bond by conjugating —OH group of hyaluronic acid and —NH2 of polyethyleneimine using CDI.

In another embodiment, the cationic polymer conjugate is prepared by conjugating hyaluronic acid or its derivative and PEI using a crosslinking agent.

The crosslinking agent is selected from the group consisting of N-(2-dimethylaminopropyl)-N'-ethylcarbodidimide) (EDC), 1-cyclohexyl-3-(2-morpholino ethyl) carbodiimide (CMC), dicyclohexyl carbodiimide (DCC), diisopropyl carbodiimide (DIC), N-ethyl-3-phenylisoxazolium-3'-sulfonate (Woodward's reagent K), and N,N'-carbonyldiimidazole, but not limited thereto.

Preferably, the crosslinking agent is EDC and further includes in combination with N-hydroxysulfosuccinimide (Sulfo-NHS), 1-hydroxybentriazolemonohydrate (HOBt), or N-Hydroxysuccinimide.

In the conjugation reaction, NaCl is further added at a suitable amount, for example 10 mM to 2 M. NaCl. NaCl helps the conjugation reaction to be performed effectively by controlling electrostatic binding between hyaluronic acid and PEI.

In the conjugation reaction, 1.5~50 weight ratio of hyaluronic acid or its derivative and 50-98.5 weight ratio of PEI are conjugated to achieve the maximum efficiency of delivering the nucleic acid into cell.

As shown in reaction scheme 1, a branch-type polyethyleneimine (bPEI) is conjugated with hyaluronic acid by using EDC.

In reaction scheme 1, x ranges 25-2200, and y ranges 25-2200.

The polymerization reaction is preformed by conjugating PEI to hyaluronic acid in a form of comb-type.

Preferably, the conjugate of hyaluronic acid and PEI is prepared by modifying hyaluronic acid with the compound having two or more carboxyl groups and then conjugating the modified hyaluronic acid and PEI. The hyaluronic acid derivative is more preferable, because it increases the introduction rate of PEI with minimizing the chemical modification of hyaluronic acid. The compound having two or more carboxyl groups includes glutamic acid, gamma-carboxyl glutamic acid, aspartic acid, and glutathione but not limited thereto.

Reaction scheme 2 shows a schematic reaction for synthesizing HA-Asp-PEI 800 by forming branch-type hyaluronic acid derivative by reacting aspartic acid to HA, and then conjugating it with PEI having 800 KD.

Reaction scheme 1

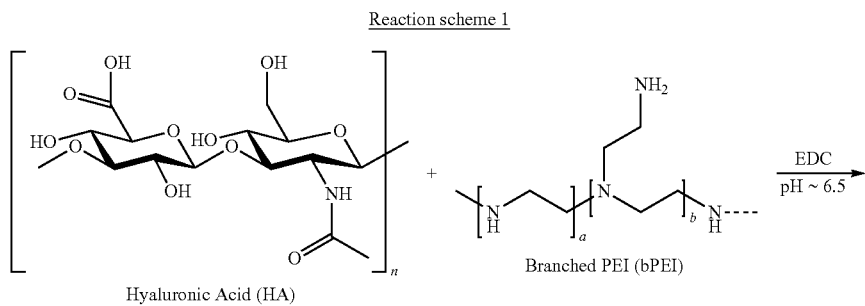

Hyaluronic Acid (HA)    Branched PEI (bPEI)

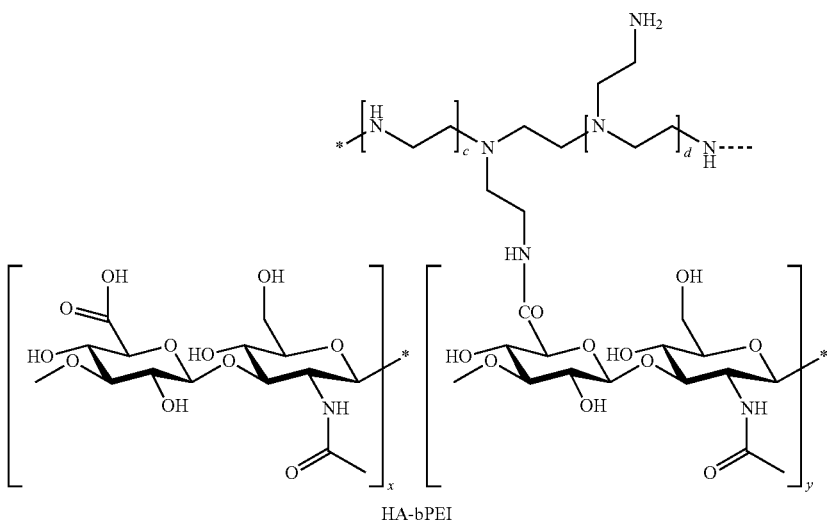

HA-bPEI

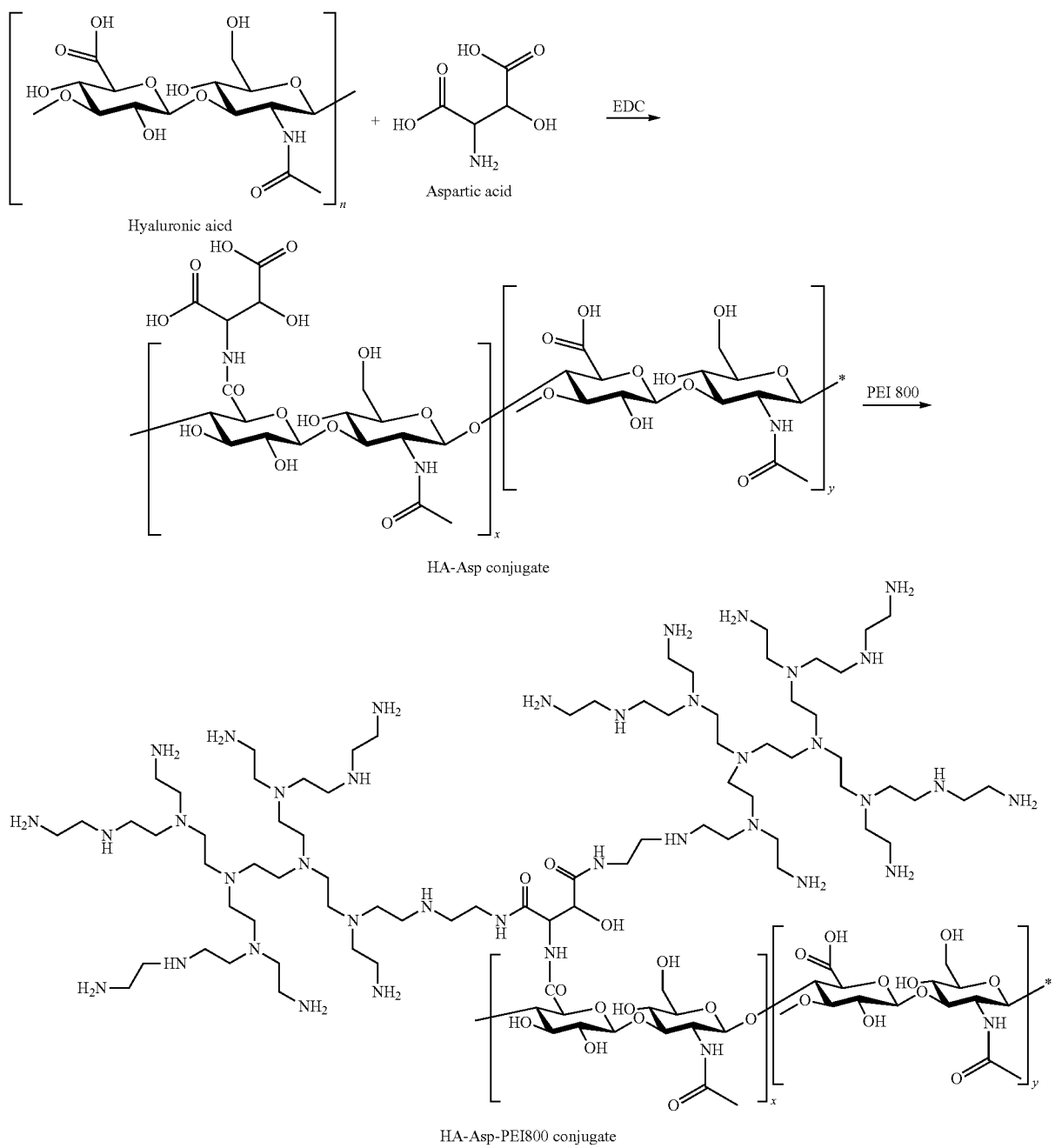

Reaction Scheme 2

HA-Asp-PEI800 conjugate

In reaction scheme, x is 25-2200, and y is 25-2200 preferably.

The mammalian cell can be any mammalian cell, as long as the cell can be introduced by siRNA or antisense nucleic acid of interest, and preferably the mammalian cell is a cancer cell. The examples of cancer cells include human lung cancer cell line (A549 cell), human cervical cancer cell line (HeLa cell), cervical cancer cell line (Caski cell), mouse melanoma cell (B16F1 cell), human liver cancer cell (Hep3B cell), and human Testicular cancer cell (LNCap cell), but not limited thereto.

An embodiment of the present invention provides a composition for delivering a nucleic acid into a mammalian cell comprising a complex where the nucleic acid is bonded to a conjugate obtained by conjugating hyaluronic acid or its derivative and PEI through electrostatic binding.

In addition, another embodiment provides a method of preparing a complex for delivering a nucleic acid into a mammalian cell comprising forming a complex by binding the cationic polymer conjugate and the nucleic acid through electrostatic binding.

PEI has a problem for practical application because it has relatively high delivering efficiency and high cytotoxicity. By binding hyaluronic acid with high biocompatibility to PEI, the conjugate can strengthen the delivering capacity of PEI with positive charge and biocompatibility of hyaluronic acid.

That is, the cationic polymer conjugate obtained by conjugating hyaluronic acid or its derivative and PEI shows lower cytotoxicity than PEI and other conventional systems for delivering nucleic acid medicines. In addition, the cationic polymer conjugate shows high efficiency of delivering nucleic acid medicine including siRNA.

In the composition, the mixing ratio of the cationic polymer conjugate and the nucleic acid can be not limited, as long as the cationic polymer conjugate can form a complex sufficiently by binding the nucleic acid. Preferably, the mixing weight ratio is 1:0.1 to 1:100.

In the composition for delivering the nucleic acid into mammalian cell, the nucleic acids can be any one, for examples, siRNA, antisense nucleic acid, plasmid DNA, and etc., as long as they can be delivered into a cell. Preferably, the examples of nucleic acid include siRNA, antisense nucleic acid, or nucleic acid aptamer of 5 to 200 base pairs length. In the case that the oligonucleic acid has a size of 200 base pairs or less, it has smaller and lower negative charge than plasmid DNA, and cannot be applied to the delivery system of plasmid DNA. The delivery composition of the present invention has higher efficiency of delivering the nucleic acid than the conventional delivery system for the nucleic acid medicine, which is proved by the experiment as appended. The delivery system for the nucleic acids having 5 to 200 bp length such as siRNA and antisense nucleic acid are provided.

An embodiment of the present invention provides a method of delivering a nucleic acid comprising formation of the complex by only mixing the cationic polymer conjugate and the nucleic acid to be delivered and administration of the complex to mammalian cell.

In the administration step of delivery, the complex with a positive charge enters into cell through endocytosis by the attraction with the cellular membrane, which is negative charge. In other words, because the cationic polymer conjugate itself functions as a carrier like liposome, the complex can enter into the mammalian cell through incubation with the complex.

In the step of formation of the complex, for example, a mixture of the oligonucleic acids such as siRNA and antisense RNA and the cationic polymer conjugate are incubated at a room temperature for 20 minutes to form the complex. The complex including the cationic polymer conjugate and the nucleic acid can be administered into all mammalian cells including a cancer cell.

To measure the capacity of the complex to deliver the nucleic acid of interest into a cell, the complexes including fluorescence-labeled dsRNA Block-IT™ (Invitrogen, USA) and various carriers are delivered into the cell, and then observed by fluorescent microscope. The cytotoxicity of complex is tested with MTT assay using tetrazolium 3-(4,5-Dimethylthiazol-2-yl)-2,5-diphenyltetrazolium bromide, and the evaluation of cell damage induced by the complex is preformed with MTT assay using lactate dehydrogenase (LDH) kit.

To test an anti-cancer activity of HA-PEI/siRNA complex on an animal model, the tumor on mouse subcutaneous tissue is induced by direct injection of B16F1 melanoma and sequential administration of HA-PEI/siRNA complex and then the change in tumor size is observed.

The method of delivering the oligonucleic acid using the cationic polymer conjugate according to the present invention increases the efficiency of delivering the nucleic acid, in comparison with the cationic polymers which has been used as conventional carriers. The method can be applied effectively for a treatment using oligonucleic acids such as siRNA, antisense RNA and etc.

As described above, the cationic polymer conjugate obtained by conjugation of the hyaluronic acid or its derivative and PEI forms a complex with nucleic acids such as siRNA, antisense nucleic acid, and etc., and improves the efficiency of delivering nucleic acid into cell with low cytotoxicity, compared to conventional carrier. Accordingly, the cationic polymer conjugate of hyaluronic acid or its derivative and PEI is a carrier of delivering nucleic acid stably and effectively into various cells, and expected to be useful for industrial applications.

The present invention is further explained in more detail with reference to the following examples. These examples, however, should not be interpreted as limiting the scope of the present invention in any manner.

Comparative Example 1

Preparation of Conventional Cationic Polymer

Cationic polymer, 25 kD PEI (Sigma-Aldrich, USA) was dissolved in water to be adjusted to 1 mM, taken 100 ml to pour to 100 mL Pyrex volumetic glass flask and was adjusted to pH 5 with the addition of 1N NaCl. For purification, the solution was passed through syringe filter with a pore of 0.2 μm, and then stored at 4° C. for subsequent use.

Comparative Example 2

Commercially-Available Cationic Polymer Liposome

Commercially available cationic polymer liposome, LipofectAMINE 2000 (Invitrogen, USA) was purchased and used according to product's manual.

Example 1

Preparation of Cationic Polymer Conjugate 25 mg of 235 kD hyaluronic acid (Lifecore Biomedical, Inc., USA) was dissolved in 20 ml water, added by 30 mg of 2.5 kD PEI (Sigma-Aldrich, USA) and then adjusted to pH 6 with 1N HCl. The resultant solution in flask was added by 0.5 mmole of N-(2-dimethylaminopropyl)-N'-ethylcarbodidimide (EDC) (Sigma-Aldrich, USA) and stirred at room temperature for 12 hours. To remove the impurities and unreacted material, the solution was dialyzed with a dialysis membrane in water. The obtained cationic polymer conjugate was stored at 4° C. for subsequent use.

Example 2

Preparation of Cationic Polymer Conjugate 25 mg of 17 kD hyaluronic acid (Lifecore Biomedical, Inc., USA) was dissolved in 20 ml water, added by 30 mg of 2.5 kD PEI (Sigma-Aldrich, USA), and then adjusted to pH 6 by 1N HCl to obtain cationic polymer conjugate according to the substantially same method of EXAMPLE 1.

Example 3

Preparation of Cationic Polymer Conjugate 25 mg of 64 kD hyaluronic acid (Lifecore Biomedical, Inc., USA) was dissolved in 20 ml water, added by 30 mg 2.5 kD PEI (Sigma-Aldrich, USA) and then adjusted to pH6 by 1N HCl. The resultant solution in flask was added by 1.0 mmole of EDC and stirred at room temperature. To remove the impurities and unreacted material, the solution was dialyzed with dialysis membrane in water. The obtained cationic polymer conjugate was stored at 4° C. for subsequent use.

Example 4

Preparation of Cationic Polymer Conjugate 25 mg of 420 kD hyaluronic acid (Lifecore Biomedical, Inc., USA) was dissolved in 20 ml water, added by 30 mg of 2.5 kD PEI (Sigma-Aldrich, USA), and then adjusted to pH 6 by 1N HCl to obtain cationic polymer conjugate according to the substantially same method of EXAMPLE 1.

Example 5

Preparation of Cationic Polymer Conjugate 25 mg of 17 kD hyaluronic acid (Lifecore Biomedical, Inc., USA) was dissolved in 20 ml water, added by 30 mg of 25 kD PEI (Sigma-Aldrich, USA), and then adjusted to pH 6 by 1N HCl to obtain cationic polymer conjugate according to the substantially same method of EXAMPLE 3.

Example 6

Preparation of Cationic Polymer Conjugate 25 mg of 64 kD hyaluronic acid (Lifecore Biomedical, Inc., USA) was dissolved in 20 ml water, added by 30 mg of 25 kD PEI (Sigma-Aldrich, USA), and then adjusted to pH 6 by 1N HCl to obtain cationic polymer conjugate according to the substantially same method of EXAMPLE 3.

Example 7

Preparation of Cationic Polymer Conjugate 25 mg of 235 kD hyaluronic acid (Lifecore Biomedical, Inc., USA) was dissolved in 20 ml water, added by 30 mg of 25 kD PEI (Sigma-Aldrich, USA), and then adjusted to pH 6 by 1N HCl to obtain cationic polymer conjugate according to the substantially same method of EXAMPLE 3.

Example 8

Preparation of Cationic Polymer Conjugate 25 mg of 420 kD hyaluronic acid (Lifecore Biomedical, Inc., USA) was dissolved in 20 ml water, added by 30 mg of 25 kD PEI (Sigma-Aldrich, USA), and then adjusted to pH 6 by 1N HCl to obtain cationic polymer conjugate according to the substantially same method of EXAMPLE 3.

Example 9

Preparation of Cationic Polymer Conjugate 25 mg of 780 kD hyaluronic acid (Lifecore Biomedical, Inc., USA) was dissolved in 20 ml water, added by 50 mg of 25 kD PEI (Sigma-Aldrich, USA), and then adjusted to pH 6 by 1N HCl to obtain cationic polymer conjugate according to the substantially same method of EXAMPLE 3.

Example 10

Preparation of Cationic Polymer Conjugate 25 mg of 17 kD hyaluronic acid (Lifecore Biomedical, Inc., USA) was dissolved in 20 ml water, added by 50 mg of 70 kD PEI (Sigma-Aldrich, USA), and then adjusted to pH 6 by 1N HCl to obtain cationic polymer conjugate according to the substantially same method of EXAMPLE 1.

Example 11

Preparation of Cationic Polymer Conjugate 25 mg of 35 kD hyaluronic acid (Lifecore Biomedical, Inc., USA) was dissolved in 20 ml water, added by 50 mg of 70 kD PEI (Sigma-Aldrich, USA), and then adjusted to pH 6 by 1N HCl to obtain cationic polymer conjugate according to the substantially same method of EXAMPLE 3.

Example 12

Preparation of Cationic Polymer Conjugate 25 mg of 64 kD hyaluronic acid (Lifecore Biomedical, Inc., USA) was dissolved in 20 ml water, added by 50 mg of 70 kD PEI (Sigma-Aldrich, USA), and then adjusted to pH 6 by 1N HCl to obtain cationic polymer conjugate according to the substantially same method of EXAMPLE 1.

Example 13

Preparation of Cationic Polymer Conjugate 25 mg of 235 kD hyaluronic acid (Lifecore Biomedical, Inc., USA) was dissolved in 20 ml water, added by 50 mg of 70 kD PEI (Sigma-Aldrich, USA), and then adjusted to pH 6 by 1N HCl to obtain cationic polymer conjugate according to the substantially same method of EXAMPLE 1.

Example 14

Preparation of Cationic Polymer Conjugate 50 mg of 420 kD hyaluronic acid (Lifecore Biomedical, Inc., USA) was dissolved in 20 ml water, added by 150 mg of 70 kD PEI (Sigma-Aldrich, USA), and then adjusted to pH 6 by 1N HCl to obtain cationic polymer conjugate according to the substantially same method of EXAMPLE 3.

Example 15

Preparation of Cationic Polymer Conjugate 25 mg of 35D hyaluronic acid (Lifecore Biomedical, Inc., USA) was dissolved in 20 ml water, added by 150 mg of 25 kD PEI (Sigma-Aldrich, USA), and then adjusted to pH 6 by 1N HCl to obtain cationic polymer conjugate according to the substantially same method of EXAMPLE 1.

Example 16

Preparation of Cationic Polymer Conjugate 25 mg of 64D hyaluronic acid (Lifecore Biomedical, Inc., USA) was dissolved in 20 ml water, added by 150 mg of 25 kD PEI (Sigma-Aldrich, USA), and then adjusted to pH 6 by 1N HCl to obtain cationic polymer conjugate according to the substantially same method of EXAMPLE 1.

Example 17

Preparation of Cationic Polymer Conjugate 25 mg of 170 kD hyaluronic acid (Lifecore Biomedical, Inc., USA) was dissolved in 20 ml water, added by 150 mg of 25 kD PEI (Sigma-Aldrich, USA), and then adjusted to pH 6 by 1N HCl to obtain cationic polymer conjugate according to the substantially same method of EXAMPLE 1.

Example 18

Preparation of Cationic Polymer Conjugate 25 mg of 235 kD hyaluronic acid (Lifecore Biomedical, Inc., USA) was dissolved in 20 ml water, added by 150 mg of 25 kD PEI (Sigma-Aldrich, USA), and then adjusted to pH 6 by 1N HCl to obtain cationic polymer conjugate according to the substantially same method of EXAMPLE 3.

Example 19

Preparation of Cationic Polymer Conjugate 25 mg of 420 kD hyaluronic acid (Lifecore Biomedical, Inc., USA) was dissolved in 20 ml water, added by 150 mg of 25 kD PEI (Sigma-Aldrich, USA), and then adjusted to pH 6 by 1N HCl to obtain cationic polymer conjugate according to the substantially same method of EXAMPLE 1.

Example 20

Preparation of Cationic Polymer Conjugate 50 mg of 780 kD hyaluronic acid (Lifecore Biomedical, Inc., USA) was dissolved in 20 ml water, added by 150 mg of 25 kD PEI (Sigma-Aldrich, USA), and then adjusted to pH 6 by 1N HCl to obtain cationic polymer conjugate according to the substantially same method of EXAMPLE 1.

Example 21

Preparation of Cationic Polymer Conjugate 25 mg of 35 kD hyaluronic acid (Lifecore Biomedical, Inc., USA) was dissolved in 20 ml water, added by 200 mg of 70 kD PEI (Sigma-Aldrich, USA), and then adjusted to pH 6 by 1N HCl to obtain cationic polymer conjugate according to the substantially same method of EXAMPLE 1.

Example 22

Preparation of Cationic Polymer Conjugate 50 mg of 64 kD hyaluronic acid (Lifecore Biomedical, Inc., USA) was dissolved in 20 ml water, added by 200 mg of 70 kD PEI (Sigma-Aldrich, USA), and then adjusted to pH 6 by 1N HCl to obtain cationic polymer conjugate according to the substantially same method of EXAMPLE 1.

Example 23

Preparation of Cationic Polymer Conjugate 25 mg of 235 kD hyaluronic acid (Lifecore Biomedical, Inc., USA) was dissolved in 20 ml water, added by 200 mg of 70 kD PEI (Sigma-Aldrich, USA), and then adjusted to pH 6 by 1N HCl to obtain cationic polymer conjugate according to the substantially same method of EXAMPLE 1.

Example 24

Preparation of Cationic Polymer Conjugate 50 mg of 780 kD hyaluronic acid (Lifecore Biomedical, Inc., USA) was dissolved in 20 ml water, added by 200 mg of 70 kD PEI (Sigma-Aldrich, USA), and then adjusted to pH 6 by 1N HCl to obtain cationic polymer conjugate according to the substantially same method of EXAMPLE 1.

Example 25

Preparation of Cationic Polymer Conjugate 25 mg of 35 kD hyaluronic acid (Lifecore Biomedical, Inc., USA) was dissolved in 20 ml water, added by 500 mg of 2.5 kD PEI (Sigma-Aldrich, USA), and then adjusted to pH 6 by 1N HCl to obtain cationic polymer conjugate according to the substantially same method of EXAMPLE 1.

Example 26

Preparation of Cationic Polymer Conjugate 50 mg of 64 kD hyaluronic acid (Lifecore Biomedical, Inc., USA) was dissolved in 20 ml water, added by 500 mg of 2.5 kD PEI (Sigma-Aldrich, USA), and then adjusted to pH 6 by 1N HCl to obtain cationic polymer conjugate according to the substantially same method of EXAMPLE 1.

Example 27

Preparation of Cationic Polymer Conjugate 25 mg of 235 kD hyaluronic acid (Lifecore Biomedical, Inc., USA) was dissolved in 20 ml water, added by 500 mg of 2.5 kD PEI (Sigma-Aldrich, USA), and then adjusted to pH 6 by 1N HCl to obtain cationic polymer conjugate according to the substantially same method of EXAMPLE 3.

Example 28

Preparation of Cationic Polymer Conjugate 50 mg of 420 kD hyaluronic acid (Lifecore Biomedical, Inc., USA) was dissolved in 20 ml water, added by 500 mg of 2.5 kD PEI (Sigma-Aldrich, USA), and then adjusted to pH 6 by 1N HCl to obtain cationic polymer conjugate according to the substantially same method of EXAMPLE 3.

Example 29

Preparation of Cationic Polymer Conjugate 25 mg of 780 kD hyaluronic acid (Lifecore Biomedical, Inc., USA) was dissolved in 20 ml water, added by 500 mg of 2.5 kD PEI (Sigma-Aldrich, USA) and then adjusted to pH6 by 1N HCl. EDC 2.0 mmole was added to the solution, and stirred in flask at room temperature. To remove impurities and unreacted material, the solution was dialyzed with dialysis membrane in water. The obtained cationic polymer conjugate was stored at 4° C. for subsequent use.

Example 30

Preparation of Cationic Polymer Conjugate 50 mg of 35 kD hyaluronic acid (Lifecore Biomedical, Inc., USA) was dissolved in 20 ml water, added by 1 g of 25 kD PEI (Sigma-Aldrich, USA), and then adjusted to pH 6 by 1N HCl to obtain cationic polymer conjugate according to the substantially same method of EXAMPLE 1.

Example 31

Preparation of Cationic Polymer Conjugate 50 mg of 64 kD hyaluronic acid (Lifecore Biomedical, Inc., USA) was dissolved in 20 ml water, added by 1 g of 25 kD PEI (Sigma-Aldrich, USA), and then adjusted to pH 6 by 1N HCl to obtain cationic polymer conjugate according to the substantially same method of EXAMPLE 1.

Example 32

Figure 1B:
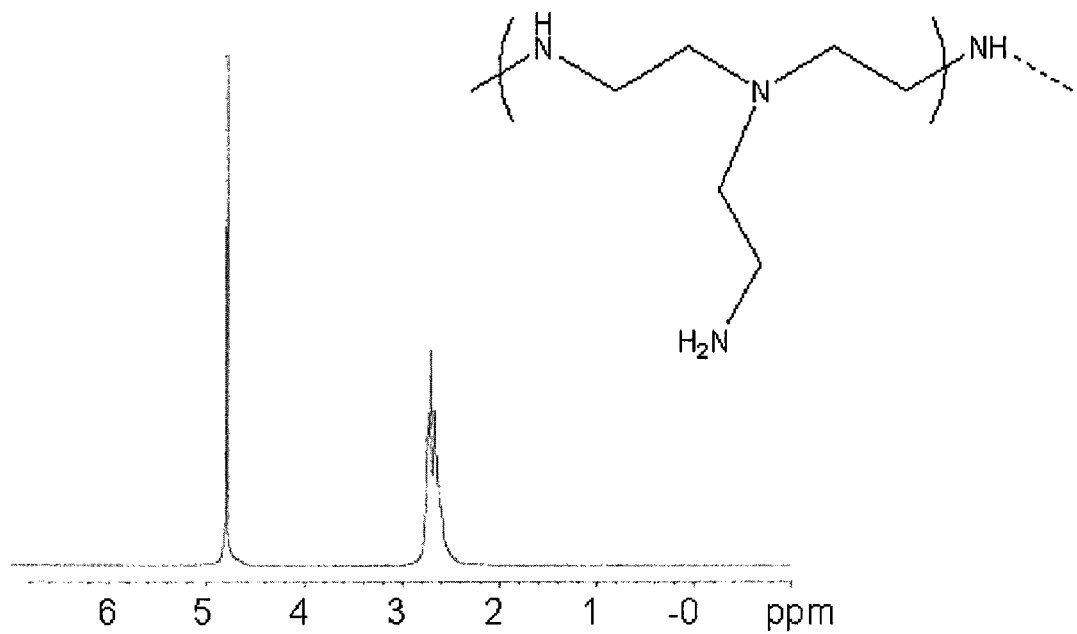
Figure 1C:
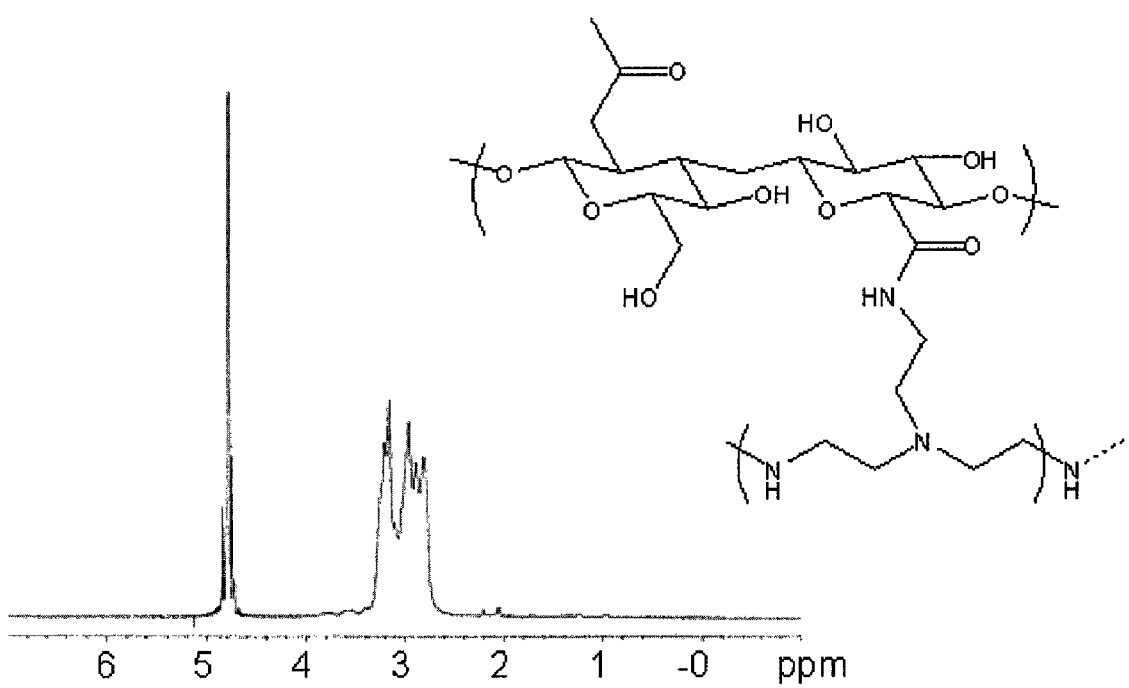

Preparation of Cationic Polymer Conjugate 50 mg of 235 kD hyaluronic acid (Lifecore Biomedical, Inc., USA) was dissolved in 20 ml water, added by 1 g of 25 kD PEI (Sigma-Aldrich, USA), and then adjusted to pH 6 by 1N HCl to obtain cationic polymer conjugate according to the substantially same method of EXAMPLE 3. The cationic polymer conjugate were analyzed with NMR spectrometry to show the result in FIG. 1A to FIG. 1C. FIGS. 1A, 1B and 1C are NMR analysis result of hyaluronic acid, polyethyleneimine, and the cationic polymer conjugate, respectively.

Example 33

Preparation of Cationic Polymer Conjugate 50 mg of 420 kD hyaluronic acid (Lifecore Biomedical, Inc., USA) was dissolved in 20 ml water, added by 1 g of 25 kD PEI (Sigma-Aldrich, USA), and then adjusted to pH 6 by 1N HCl to obtain cationic polymer conjugate according to the substantially same method of EXAMPLE 29.

Example 34

Preparation of Cationic Polymer Conjugate 100 mg of 780 kD hyaluronic acid (Lifecore Biomedical, Inc., USA) was dissolved in 20 ml water, added by 1.5 g of 25 kD PEI (Sigma-Aldrich, USA), and then adjusted to pH 6 by 1N HCl to obtain cationic polymer conjugate according to the substantially same method of EXAMPLE 29.

Example 35

Preparation of Cationic Polymer Conjugate 100 mg of 17 kD hyaluronic acid (Lifecore Biomedical, Inc., USA) was dissolved in 20 ml water, added by 1.5 g of 70 kD PEI (Sigma-Aldrich, USA), and then adjusted to pH 6 by 1N HCl to obtain cationic polymer conjugate according to the substantially same method of EXAMPLE 1.

Example 36

Preparation of Cationic Polymer Conjugate 100 mg of 35 kD hyaluronic acid (Lifecore Biomedical, Inc., USA) was dissolved in 20 ml water, added by 1.5 g of 70 kD PEI (Sigma-Aldrich, USA), and then adjusted to pH 6 by 1N HCl to obtain cationic polymer conjugate according to the substantially same method of EXAMPLE 1.

Example 37

Preparation of Cationic Polymer Conjugate 100 mg of 64 kD hyaluronic acid (Lifecore Biomedical, Inc., USA) was dissolved in 20 ml water, added by 1.5 g of 70 kD PEI (Sigma-Aldrich, USA), and then adjusted to pH 6 by 1N HCl to obtain cationic polymer conjugate according to the substantially same method of EXAMPLE 3.

Example 38

Preparation of Cationic Polymer Conjugate 100 mg of 235 kD hyaluronic acid (Lifecore Biomedical, Inc., USA) was dissolved in 20 ml water, added by 1.5 g of 70 kD PEI (Sigma-Aldrich, USA), and then adjusted to pH 6 by 1N HCl to obtain cationic polymer conjugate according to the substantially same method of EXAMPLE 3.

Example 39

Preparation of Cationic Polymer Conjugate 100 mg of 420 kD hyaluronic acid (Lifecore Biomedical, Inc., USA) was dissolved in 20 ml water, added by 1.5 g of 70 kD PEI (Sigma-Aldrich, USA), and then adjusted to pH 6 by 1N HCl to obtain cationic polymer conjugate according to the substantially same method of EXAMPLE 29.

Example 40

Preparation of Cationic Polymer Conjugate 100 mg of 780 kD hyaluronic acid (Lifecore Biomedical, Inc., USA) was dissolved in 20 ml water, added by 1.5 g of 70 kD PEI (Sigma-Aldrich, USA), and then adjusted to pH 6 by 1N HCl to obtain cationic polymer conjugate according to the substantially same method of EXAMPLE 29.

25 mg of 235 kD hyaluronic acid (Lifecore Biomedical, Inc., USA) was dissolved in 20 ml water in 250 mL pyrex, round-bottom flask, added by 30 mg of 2.5 kD PEI (Sigma-Aldrich, USA) and then adjusted to pH6 by 1N HCl. The resultant solution was added by 0.5 mmole of EDC and stirred at room temperature for 12 hours. To remove the impurities and unreacted material, the solution was dialyzed with dialysis membrane in water. The obtained cationic polymer conjugate was stored at 4° C. for subsequent use.

Example 41

Preparation of Cationic Polymer Conjugate 50 mg of 234 kD hyaluronic acid (Lifecore Biomedical, Inc., USA) was dissolved in 20 ml water in 250 mL pyrex volumetric round-bottom flask, added by 200 ml of tetrahydrofuran (THF). The resultant solution was added by 0.5 mmole of N,N-carbonyldiimidazole (CDI, Sigma-Aldrich, USA) and stirred at 37° C. for 1 hour. 500 mg of 25 kD PEI (Sigma-Aldrich, USA) was dissolved in the hyaluronic acid solution, adjusted to pH6 by 1N HCl, and then stirred at 37° C. for 12 hours. To remove the impurities and unreacted material, the solution was dialyzed with dialysis membrane in water. The obtained cationic polymer conjugate was stored at 4° C. for subsequent use.

Example 42

Preparation of Cationic Polymer Conjugate 50 mg of 234 kD hyaluronic acid (Lifecore Biomedical, Inc., USA) was dissolved in 20 ml water in 250 mL pyrex, round-bottom flask, added by 200 ml of tetrahydrofuran (THF). 0.5 mmole of N,N-carbonyldiimidazole (CDI, Sigma-Aldrich, USA) was added to the solution, and stirred at 37° C. for 1 hour. 1 g of 25 kD PEI (Sigma-Aldrich, USA) was dissolved the hyaluronic acid solution, and adjusted to pH 6 by 1N HCl to obtain the cationic polymer conjugate according to the substantially same method of EXAMPLE 41.

Example 43

Preparation of Cationic Polymer Conjugate 50 mg of 17 kD hyaluronic acid (Lifecore Biomedical, Inc., USA) was dissolved in 20 ml water in 250 mL pyrex, round-bottom flask, added by 200 ml of tetrahydrofuran (THF). 0.5 mmole of N,N-carbonyldiimidazole (CDI, Sigma-Aldrich, USA) was added to the solution, and stirred at 37° C. for 1 hour. 500 mg of 25 kD PEI (Sigma-Aldrich, USA) was dissolved the hyaluronic acid solution, and adjusted to pH 6 by 1N HCl to obtain the cationic polymer conjugate according to the substantially same method of EXAMPLE 41.

Example 44

Preparation of Cationic Polymer Conjugate 50 mg of 17 kD hyaluronic acid (Lifecore Biomedical, Inc., USA) was dissolved in 20 ml water in 250 mL pyrex, round-bottom flask, added by 200 ml of tetrahydrofuran (THF). 0.5 mmole of N,N-carbonyldiimidazole (CDI, Sigma-Aldrich, USA) was added to the solution, and stirred at 37° C. for 1 hour. 1 g of 25 kD PEI (Sigma-Aldrich, USA) was dissolved the hyaluronic acid solution, and adjusted to pH 6 by 1N HCl to obtain the cationic polymer conjugate according to the substantially same method of EXAMPLE 41.

Example 45

Preparation of Cationic Polymer Conjugate

The hyaluronic acid-polyethyleneimine conjugate was prepared by conjugating amine group of PEI and carboxyl group of HA via amide bond. The weight ratios of PEI to HA were 1:2, 1:5, and 1:20. The experiment method is described for the case that the weight ratio of PEI to HA was 1:20 in detail.

20 mg of 130 kD hyaluronic acid was dissolved in 10 mL water, and added by 10 mL of 40 mg/mL 25 kD PEI. Because the precipitates formed by charge interaction between HA and PEI, NaCl was added to 250 mM to 1M of final concentration, and then adjusted to pH 6.5 by addition of 1 M HCl. EDC hydrochloride 40.4 mg and HOBt 28.5 mg were dissolved in 500 μL distilled water and 500 μL DMSO, and added to HA and PEI aqueous solution to induce the reaction. After 24 hours, the reaction was quenched by increasing pH to 7.0 with addition of 1M NaOH, dialyzed with dialysis membrane (MWCO: 10 kDa) in 250 mM NaCl aqueous solution for 2 days, and then dialyzed with decreasing the concentration of NaCl gradually. Finally, the dialysis was performed in distilled water for a day to remove the impurities.

The HA-PEI conjugate was analyzed with gel permeation chromatography (GPC) under the following condition: Waters 1525 binary HPLC pump, Waters 2487 dual λ absorbance detector, Waters 717 plus autosampler, Ultrahydrogel 1000 column (7.8 mm×30 cm) (Milford, Mass., USA). Elution solution was a solution mixed with 34 mM phosphate buffer (pH 6.6) and 20% methanol, and flow rate was 1.0 mL/min. GPC analysis result were shown in FIG. 2.

Figure 2:
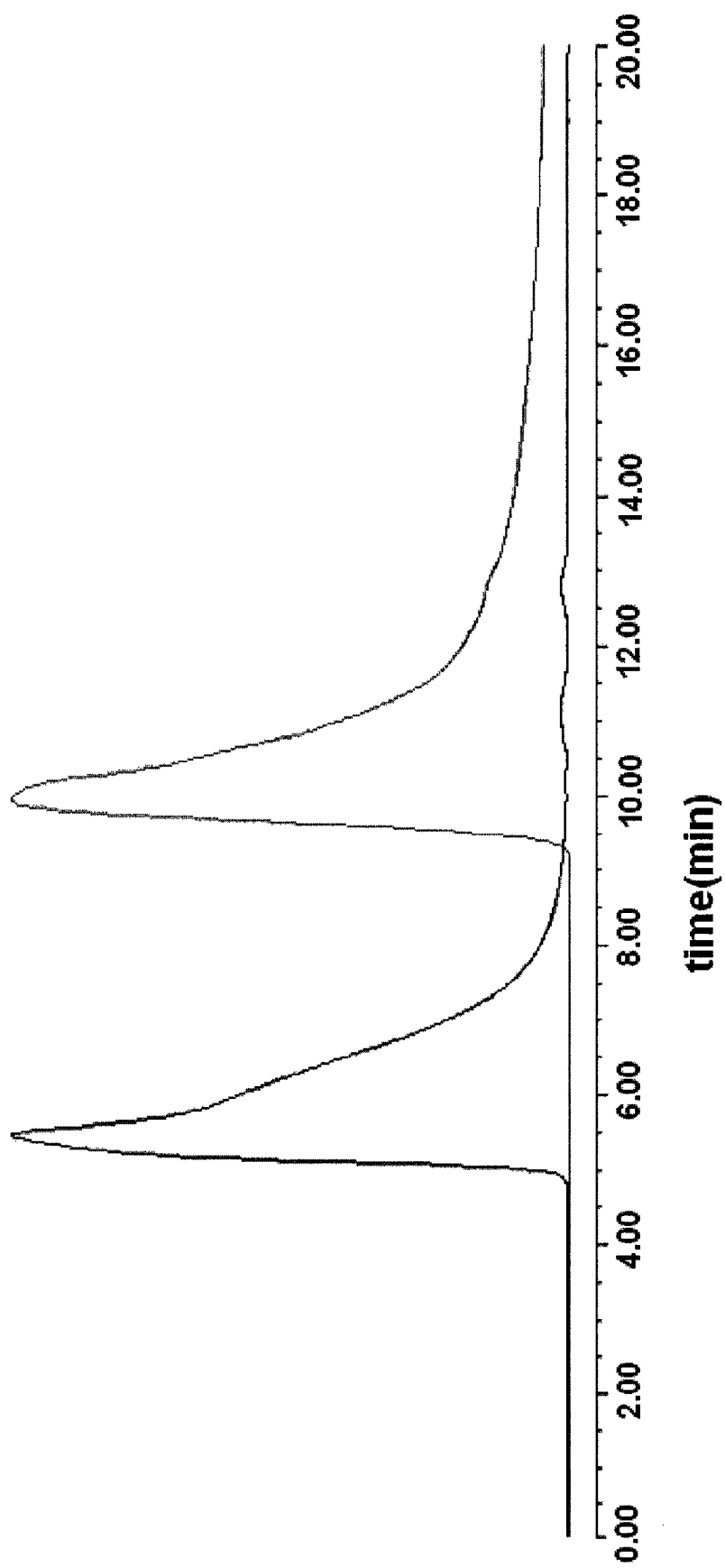
FIG. 2 is RP-HPLC result of HA-branched PEI (bPEI) at 210 nm, and left side for HA before reaction and right side for PEI-HA.

FIG. 2 is an RP-HPLC result of HA-branched PEI (bPEI) at wavelength of 210 nm, and left side for HA before reaction and right side for PEI-HA. As the molecular weight of HA-PEI conjugate increased after synthesis, the time for peak was longer and other impurities was not found.

Figure 3:
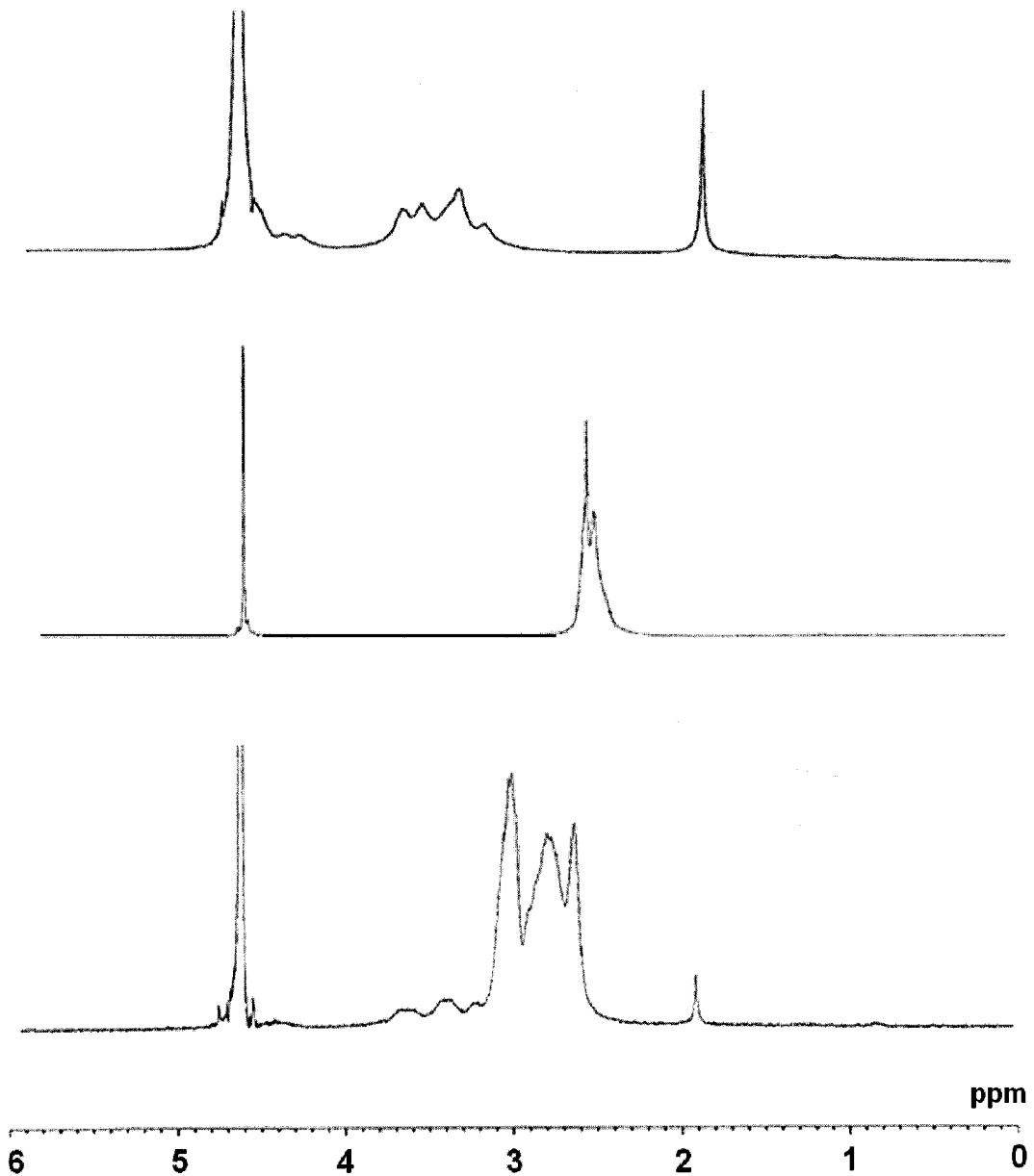
FIG. 3 is $^1$H NMR result of HA-bPEI in (A) HA before reaction, (B) PEI before reaction, and (C) HA-PEI prepared in Example 45.

Modification rate of ADH in HA-ADH was analyzed with $^1$H NMR spectrometer (DPX300, Bruker, Germany) to show the result in FIG. 3. FIG. 3 is $^1$H NMR result of HA-bPEI in (A) HA before reaction, (B) PEI before reaction, and (C) HA-PEI. In comparison with $^1$H NMR spectra of HA and PEI, the spectrum of PEI-HA conjugate showed that methyl peak of acetoamide in HA at 1.9 ppm and PEI peak at 2.5~3.2 ppm shifted to 2.5 ppm. According to the integral value of the peak, 5.7, 11.4, and 24.2 mol % of carboxyl group were bonded to PEI at 1:2, 1:5, and 1:20 of weight ratios of PEI to HA, respectively.

Example 46

Preparation and Analysis of HA-Aspartic Acid

Figure 4:
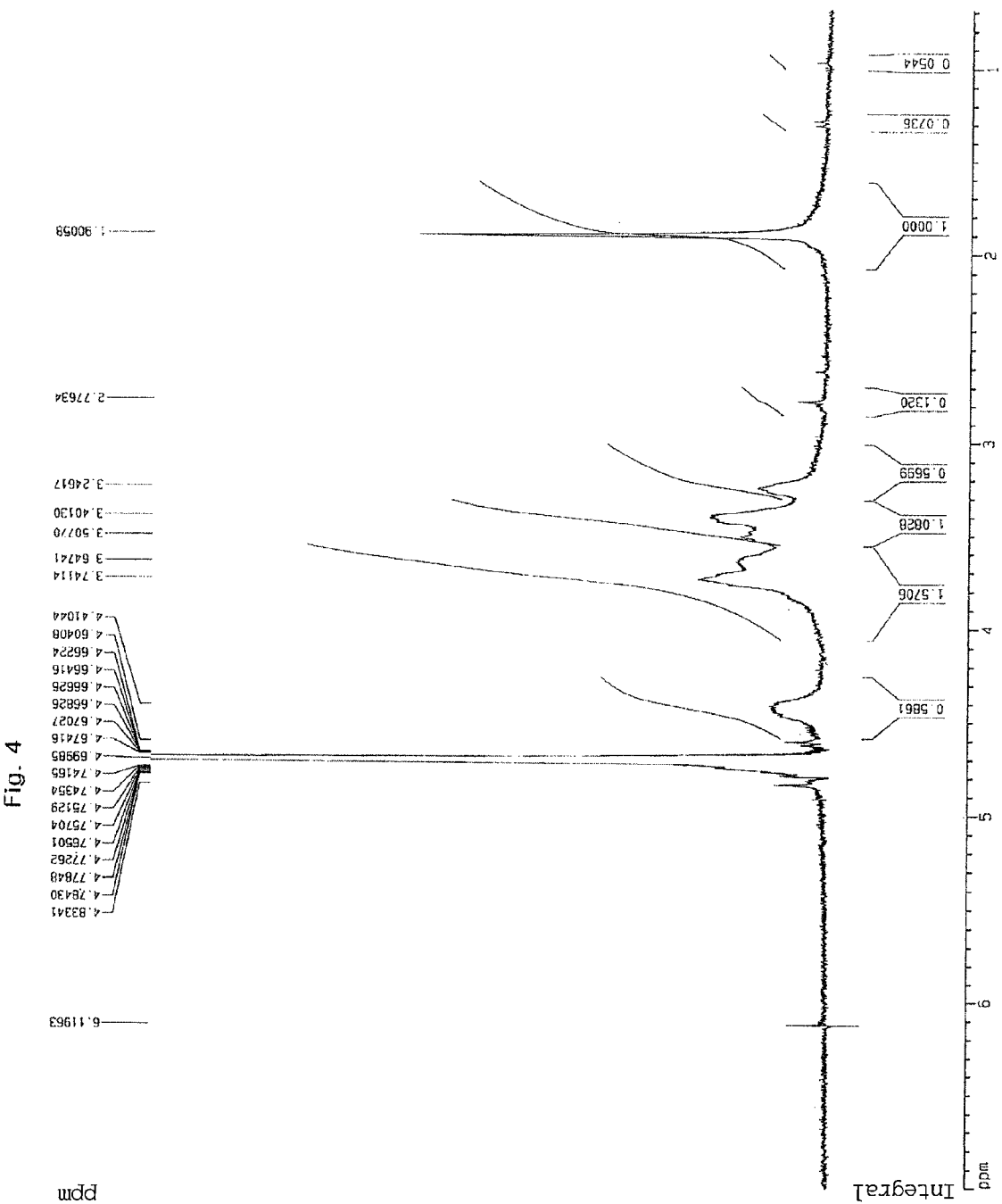
FIG. 4 is $^1$H NMR result of HA-Aspartic acid obtained in Example 46, which shows 20% of substitution rate.

To increase the density of PEI with a low molecular weight which was bonded to HA, the amine group of Aspartic acid having two carboxyl groups was bonded to the carboxyl group of HA. 20 mg of hyaluronic acid was dissolved in 10 ml, added by 38.3 mg EDC and 108.5 mg of sulfo NHS, and then adjusted to pH6.0 to activate the carboxyl group of HA for 30 minutes. Then, 2-mercaptoethanol 10 μl was added to inactivate EDC, and mixed with 5 ml solution of 66.6 mg Aspartic acid dissolved in water to begin the reaction. After 6 hours, the reaction was quenched by increasing pH to 7, and the impurities were removed by dialysis tube (M.W.C.O. 3000) for 5 days. To calculate the modification rate, the product was analyzed with $^1$H NMR spectrometer according to the method of EXAMPLE 45 to show the result in FIG. 4. About 20% of carboxyl group were substituted.

Example 47

Preparation and Analysis Ha-Glutathione-PEI

To synthesize HA-Glutathine, glutathione instead of HA-AEMA was added at the same amount of the double bond of AEMA, and treated with an excessive amount of Tris(2-Carboxyethyl) phosphine Hydrochloride (TCEP) as a reducing agent. Michael addition reaction was preformed at pH 8.5 overnight, and then the impurities were removed with PD-10 column. The synthesized HA-Glutathione was added by the same amount of PEI having a low molecular weight as the amount of glutathione and synthesized with EDC and HOB according to the method of EXAMPLE 62.

Figure 5A:
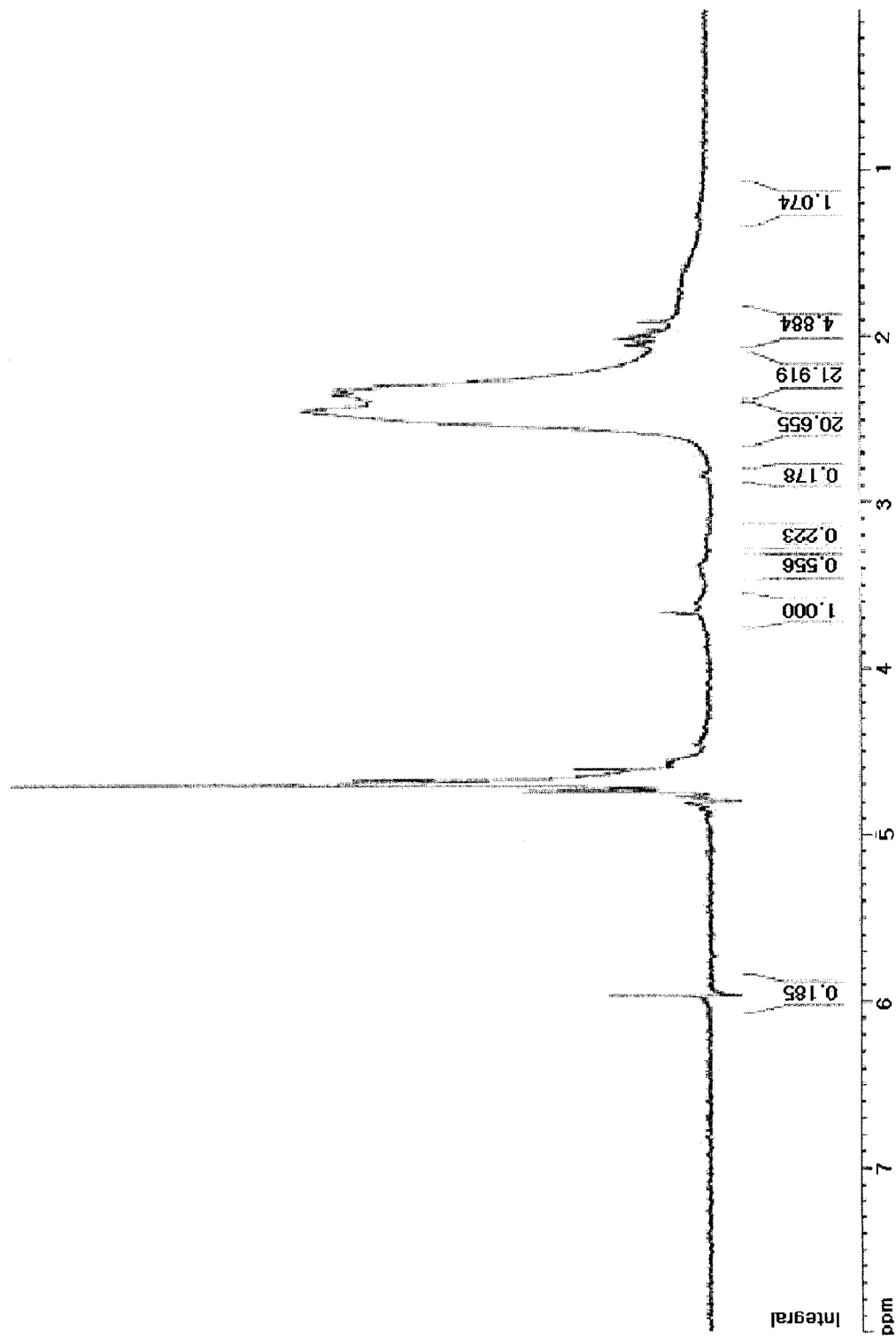
FIG. 5A to 5B are $^1$H NMR results of HA-Glutathione and HA-Glutathione-PEI obtained in Example 47; (A) HA-Glutathione and (B) HA-Glutathione-PEI.
Figure 5B:
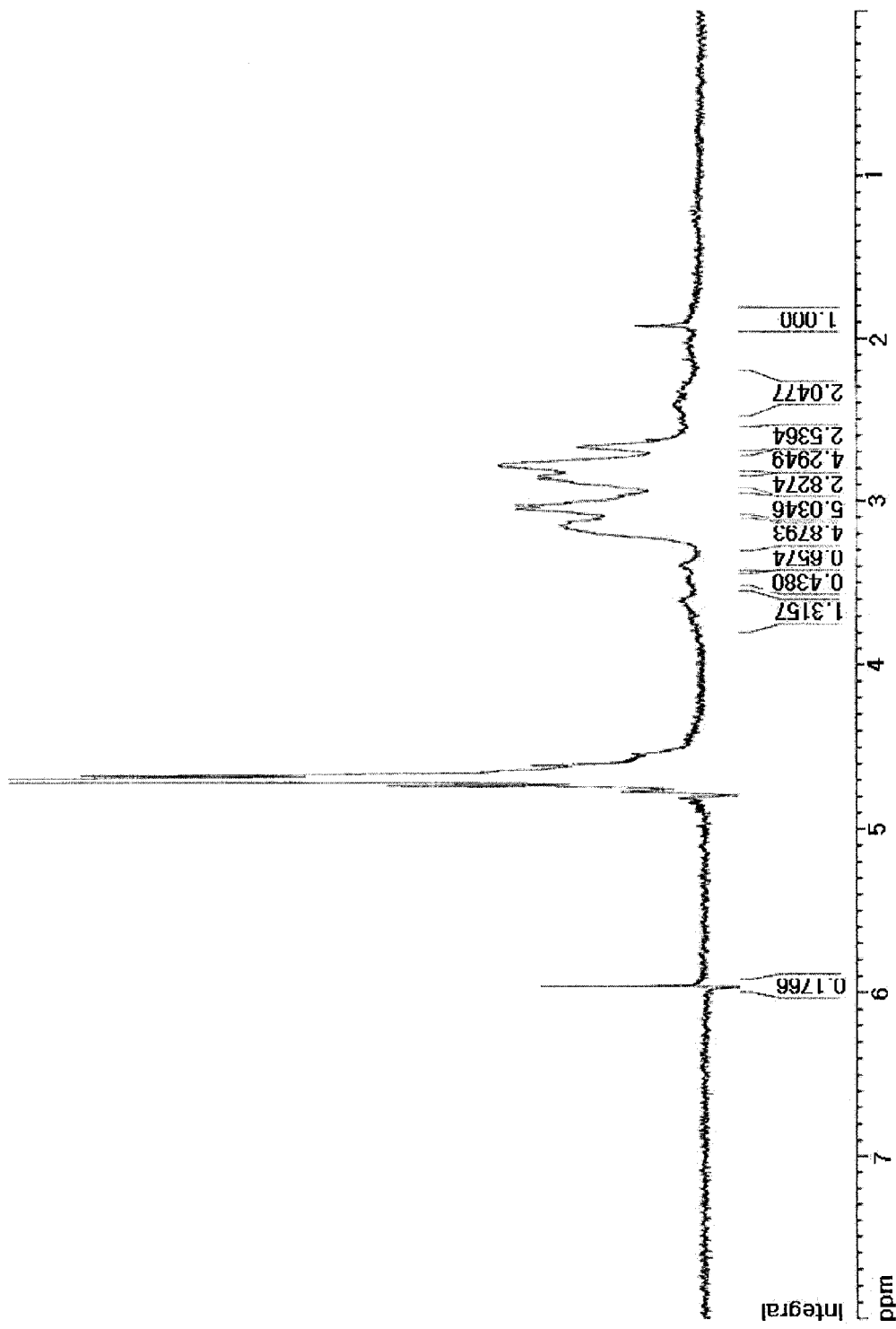

According to the method of EXAMPLE 45, the synthesized HA-Glutathione-PEI was analyzed with $^1$H NMR spectrometry to show the result in FIGS. 5A and 5B. FIGS. 5A and 5B are $^1$H NMR results of HA-Glutathione and HA-Glutathione-PEI; (A) HA-Glutathione and (B) HA-Glutathione- PEI. When calculating according to the method of EXAMPLE 62, 38.6% of carboxyl groups in HA-Glutathione were bonded.

Example 48

Measurement of Particle Size of siRNA/PEI-HA Complex siRNA/PEI-HA complex was obtained by reacting anti-PGL3-Luc siRNA (0.75 μg/L) and PEI-HA solution (2.6 μg/L) at room temperature for 15 minutes. The weight ratio of PEI-HA to siRNA ranged from 1.7 to 6.9 and the solution was added by NaCl to be 150 mM of the final concentration.

Figure 6:
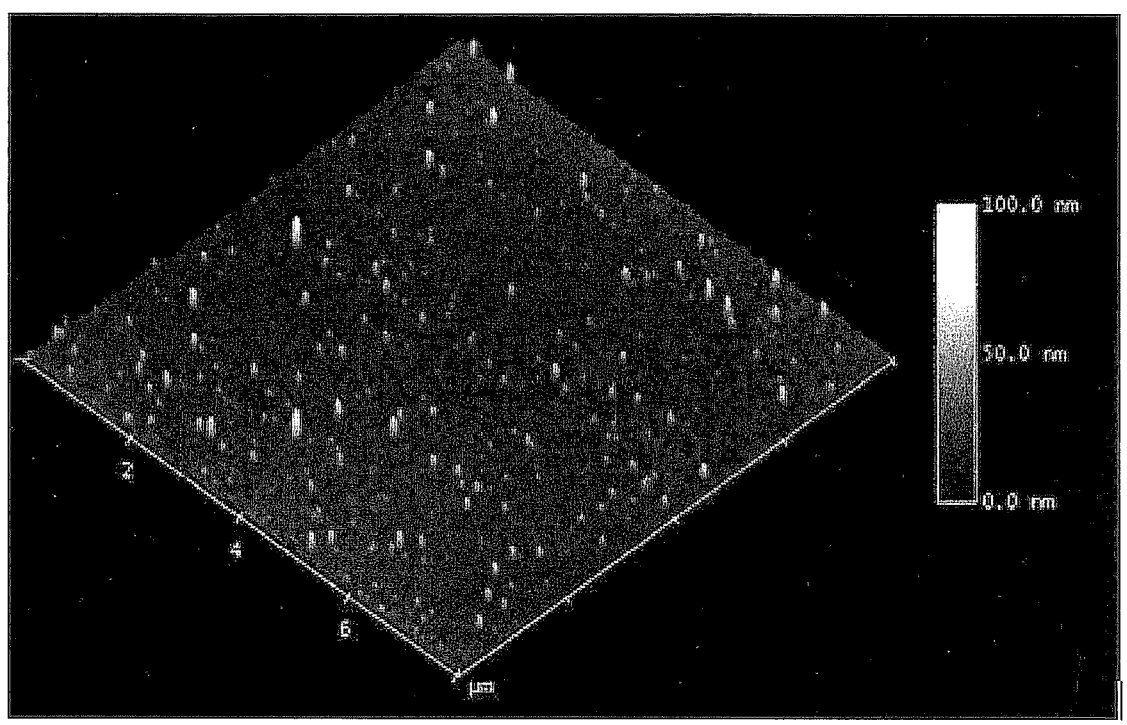
FIG. 6 is AFM result of a complex of HA-PEI conjugate and siRNA.

To analyze the physical properties of siRNA/PEI-HA complex, the prepared siRNA/PEI-HA complex solution was diluted with 750 μL distilled water and zeta-potential of siRNA/PEI-HA complex (weight ratio of PEI to HA was 1:5.2.) were measured with particle analyzer (Zetasizer Nano, MALVERN Instrument Co., UK). As a result, the weigh ratios of PEI-HA to siRNA increased as 1.7, 3.4, 5.2, and 6.9, the zeta-potentials of the complex were −21.5, −19.93, −17.07, and −15.33 mV, respectively, which confirmed that siRNA and PEI of PEI-HA conjugate formed core-shell structure by electric attraction. In addition, the size of siRNA/PEI-HA complex was measured by AFM (Multimode 3100, VEECO Instrument Co., NY, USA). The siRNA/PEI-HA complex solution (50 μL) was dispersed on silicone wafer and dried in air. AFM system was used in tapping mode at 8×8 μm scanning region. FIG. 6 showed an AFM result of a complex of HA-PEI conjugate and siRNA. According to FIG. 6, the complex had nano-sized particle of about average diameter of 21 nm.

Example 49

Cell Culture

A549, HeLa, B16F1, Hep3B, and LNCaP cell lines were purchased from American Type Culture Collection (ATCC, USA). Hep3B cell lines was cultured in Dulbecco's modified eagles medium (DMEM) (Gibco, USA) containing 10 w/v % of fetal bovine serum (HyClone laboratories Inc, USA) and 100 unit/ml of penicillin or 100 μg/ml of streptomycin. A549, B16F1, HeLa and LNCaP cell lines were cultured in RPMI 1640 (Gibco, USA) containing 10 w/v % of fetal bovine serum, penicillin, and streptomycin.

Example 50

Evaluation of Efficiency of Delivering siRNA in A549 Cell Line

Before a day, A549 cell lines were seed to 24-well plate at a concentration of 1×10⁵ cells/well. When the cells grew in each plate uniformly to be about 60-70% o, the culture medium in the plate were removed and then added with new medium at 500 μl/well. 50 μl of culture medium without the fetal bovine serum was poured to eppendorf tube, and were added with 1 μl of Block-iT (20 μmol, Invitrogen, USA) which was siRNA labeled with fluorescent marker, and cationic polymer conjugate 1-50 μl of COMPARATIVE EXAMPLE 1 and EXAMPLE 1, respectively. The solution was mixed with slow pipetting and left at room temperature for 20 minutes. The obtained complex was added to the 24-well plate and cultured in CO₂ incubator at 37° C. for 24 hours. The medium of cultured cell was replaced with new medium at 500 μl/well and then observed with fluorescence microscope to analyze the efficiency of delivering gene.

Figure 7:
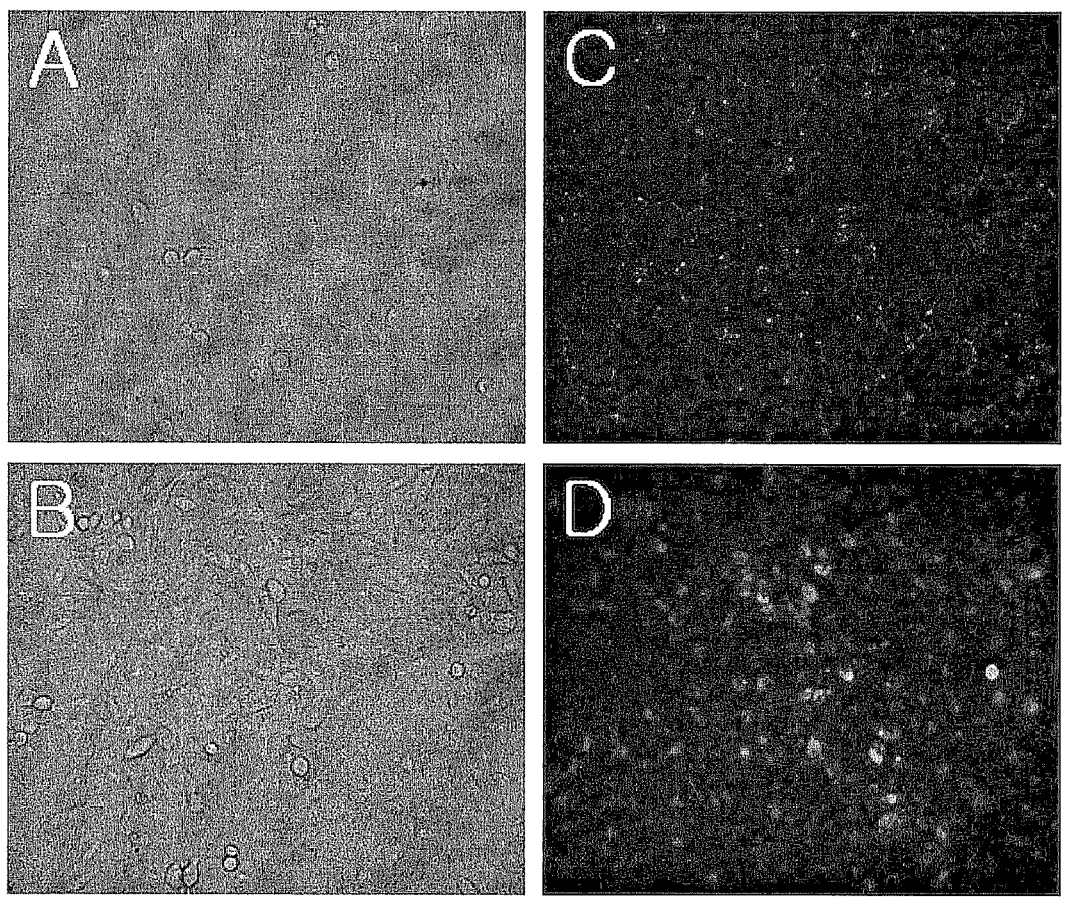
FIG. 7 shows the efficiency of delivering RNA by using cationic polymer conjugates obtained in Example 1 and Comparative Example 1 with a confocal microscope and a fluorescent microscope.

FIG. 7 shows the delivering efficiency of ribonucleic acid by cationic polymer conjugates obtained in Example 1 and Comparative Example 1 with confocal microscope and fluorescent microscope. Specifically, (A) part of FIG. 7 was treated by the polymer conjugate obtained from Comparative Example 1 and then analyzed with confocal microscope, and (B) part was treated by the polymer conjugate obtained from Example 1 and then analyzed with confocal microscope. Part (C) of FIG. 7 is a picture of fluorescent microscope showing the delivery efficiency of siRNA which was treated with the complex of the cationic polymer conjugates obtained Comparative Example 1. Part (D) is a picture of fluorescent microscope showing the delivery efficiency of siRNA which was treated with the complex conjugates obtained Example 1. As shown in FIG. 7, HA-PEI conjugate of EXAMPLE 1 delivered siRNA more effectively in A549 cell than PEI of Comparative Example 1.

Example 51

Evaluation of Delivery Efficiency of siRNA in HeLa Cell Line

Before a day, HeLa cell lines were seed to 24-well plate at a concentration of 1×10⁵ cells/well. When the cells grew uniformly in each plate to be about 60-70%, the culture medium in the plate were removed and then added with new medium at 500 μl/well. 50 μl of culture medium without the fetal bovine serum was poured to eppendorf tube, and were added with 1 μl of Block-iT (20 μmol, Invitrogen, USA) which was siRNA labeled with fluorescent marker, and cationic polymer conjugate 1-50 μl of COMPARATIVE EXAMPLE 1 and EXAMPLE 3, respectively. The solution was mixed with slow pipetting and left at room temperature for 20 minutes. The obtained complex was added to the 24-well plate and cultured in CO₂ incubator at 37° C. for 24 hours. The medium of cultured cell was replaced with new medium at 500 μl/well and then observed with fluorescence microscope to analyze the efficiency of delivering a gene.

Figure 8:
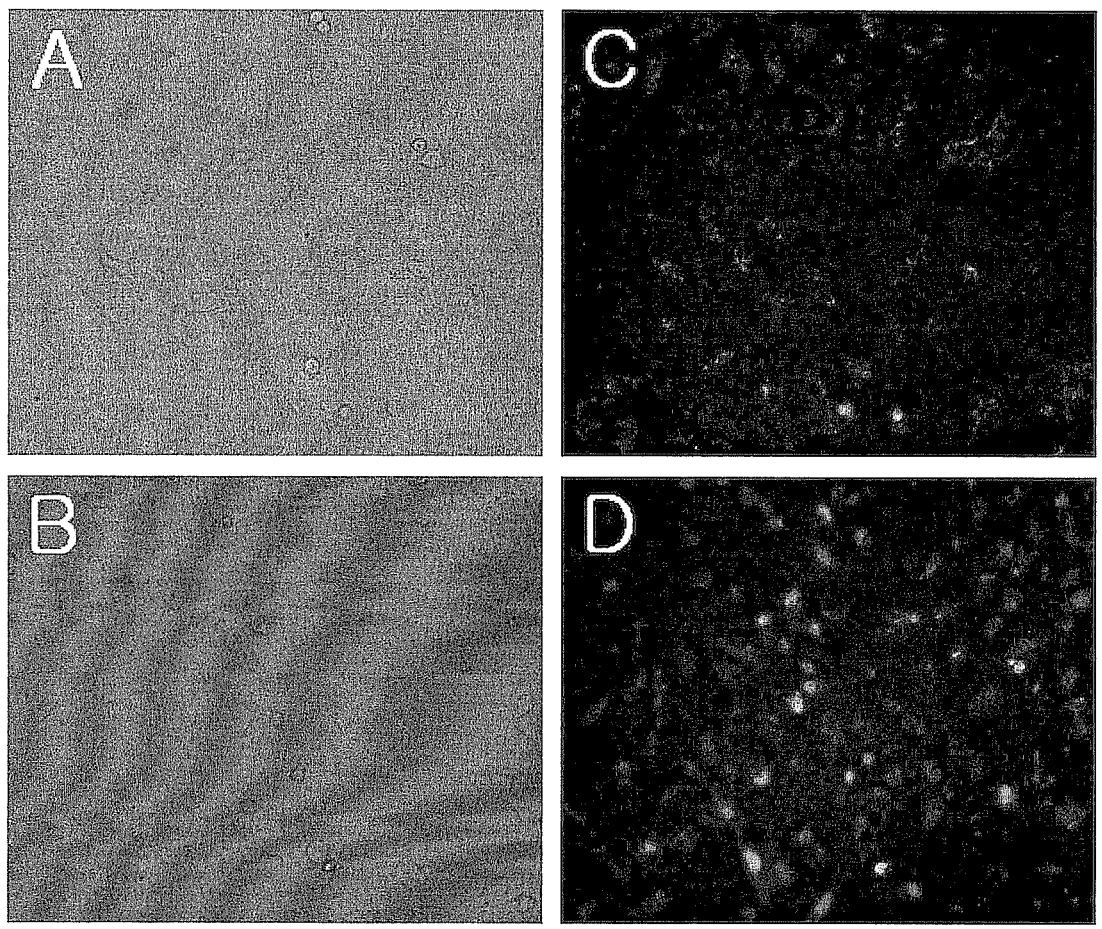
FIG. 8 shows the efficiency of delivering RNA by using cationic polymer conjugates obtained in Example 3 and Comparative Example 1 with a confocal microscope and a fluorescent microscope.

FIG. 8 shows the delivering efficiency of ribonucleic acid by cationic polymer conjugates obtained in Example 3 and Comparative Example 1 with confocal microscope and fluorescent microscope. Specifically, (A) part of FIG. 8 is a picture of fluorescent microscope obtained by treating with the polymer conjugate of Comparative Example 1 and then analyzing with confocal microscope, and (B) part is picture of fluorescent microscope obtained by treating with the polymer conjugate of Example 3 and then analyzing with confocal microscope. Part (C) of FIG. 8 is a picture of fluorescent microscope showing the delivery efficiency of siRNA which was treated with the complex of the cationic polymer conjugates obtained Comparative Example 1. Part (D) is a picture of fluorescent microscope showing the delivery efficiency of siRNA which was treated with the complex of the cationic polymer conjugates obtained Example 3. As shown in FIG. 8, HA-PEI conjugate of EXAMPLE 3 delivered siRNA more effectively in HeLa cell than PEI of Comparative Example 1.

Example 52

Evaluation of Delivery Efficiency of siRNA in B16F1 Cell Line

Before a day, B16F1 cell lines were seed to 24-well plate at a concentration of 1×10⁵ cells/well. When the cells grew uniformly in each plate to be about 60-70%, the culture medium in the plate were removed and then added with new medium at 500 µl/well. 50 µl of culture medium without the fetal bovine serum was poured to eppendorf tube, and were added with 1 µl of Block-iT (20 µmol, Invitrogen, USA) which was siRNA labeled with fluorescent marker, and cationic polymer conjugate 1-50 µl of COMPARATIVE EXAMPLE 1 and EXAMPLE 9, respectively. The solution was mixed with slow pipetting and left at room temperature for 20 minutes. The obtained complex was added to the 24-well plate and cultured in $CO_2$ incubator at 37° C. for 24 hours. The medium of cultured cell was replaced with new medium at 500 µl/well and then observed with fluorescence microscope to analyze the efficiency of delivering a gene.

Figure 9:
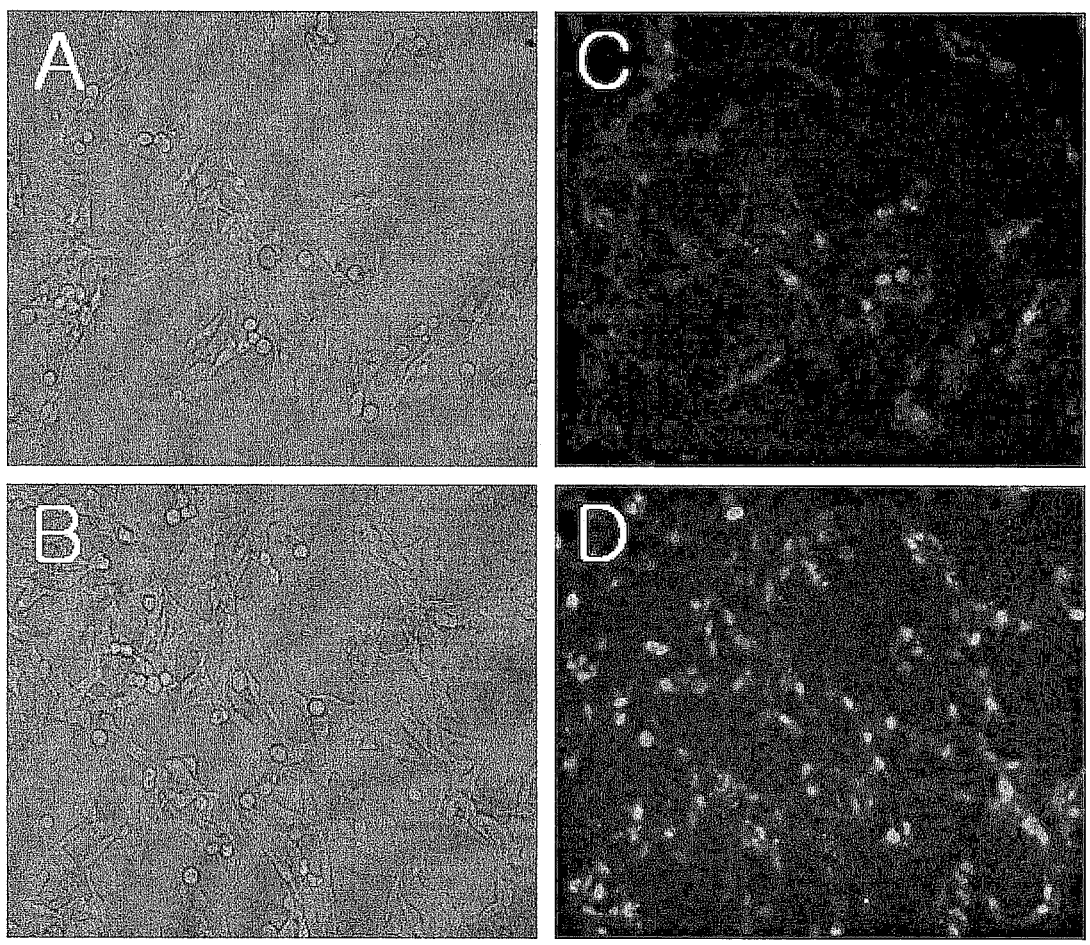
FIG. 9 shows the efficiency of delivering RNA by using cationic polymer conjugates obtained in Example 9 and Comparative Example 1 with confocal microscope and fluorescent microscope.

FIG. 9 shows the delivering efficiency of ribonucleic acid by cationic polymer conjugates obtained in Example 9 and Comparative Example 1 with confocal microscope and fluorescent microscope. Specifically, (A) part of FIG. 9 is picture of fluorescent microscope obtained by treating with the polymer conjugate of Comparative Example 1 and then analyzing with confocal microscope, and (B) part is a picture of fluorescent microscope obtained by treating with the polymer conjugate of Example 9 and then analyzing with confocal microscope. Part (C) of FIG. 9 is a picture of fluorescent microscope showing the delivery efficiency of siRNA which was treated with the complex of the cationic polymer conjugates obtained Comparative Example 1. Part (D) is a picture of fluorescent microscope showing the delivery efficiency of siRNA which was treated with the complex of the cationic polymer conjugates obtained Example 9. As shown in FIG. 9, HA-PEI conjugate of EXAMPLE 9 delivered siRNA more effectively in B16F1 cell than PEI of Comparative Example 1.

Example 53

Evaluation of Delivery Efficiency of siRNA in Hep3B Cell Line

Before a day, Hep3B cell lines were seed to 24-well plate at a concentration of $1 \times 10^5$ cells/well. When the cells grew uniformly in each plate to be about 60-70%, the culture medium in the plate were removed and then added with new medium at 500 µl/well. 50 µl of culture medium without the fetal bovine serum was poured to eppendorf tube, and were added with 1 µl of Block-iT (20 µmol, Invitrogen, USA) which was siRNA labeled with fluorescent marker, and cationic polymer conjugate 1-50 µl of Comparative Example 1 and Example 19, respectively. The solution was mixed with slow pipetting and left at room temperature for 20 minutes. The obtained complex was added to the 24-well plate and cultured in $CO_2$ incubator at 37° C. for 24 hours. The medium of cultured cell was replaced with new medium at 500 µl/well and then observed with fluorescence microscope to analyze the efficiency of delivering a gene.

Figure 10:
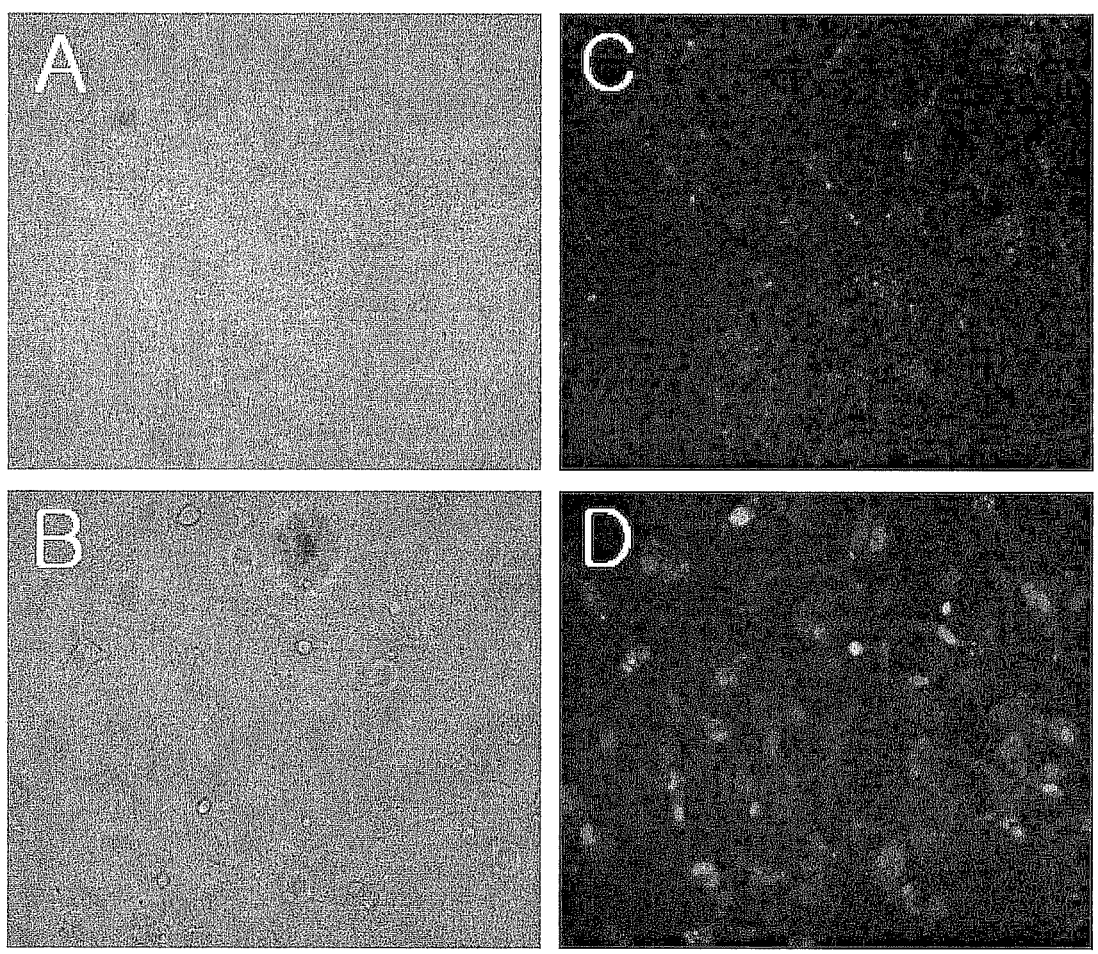
FIG. 10 shows the efficiency of delivering RNA by using cationic polymer conjugates obtained in Example 19 and Comparative Example 1 with confocal microscope and fluorescent microscope.

FIG. 10 shows the delivering efficiency of ribonucleic acid by cationic polymer conjugates obtained in Example 19 and Comparative Example 1 with confocal microscope and fluorescent microscope. Specifically, (A) part of FIG. 10 is a picture of fluorescent microscope obtained by treating with the polymer conjugate of Comparative Example 1 and then analyzed with confocal microscope, and (B) part is a picture of fluorescent microscope obtained by treating with the polymer conjugate of Example 19 and then analyzed with confocal microscope. Part (C) of FIG. 10 is a picture of fluorescent microscope showing the delivery efficiency of siRNA which was treated with the complex of the cationic polymer conjugates obtained Comparative Example 1. Part (D) is a picture of fluorescent microscope showing the delivery efficiency of siRNA which was treated with the complex of the cationic polymer conjugates obtained Example 19. As shown in FIG. 10, HA-PEI conjugate of EXAMPLE 19 delivered siRNA more effectively in Hep3B cell than PEI of Comparative Example 1.

Example 54

Evaluation of Delivery Efficiency of siRNA in LNCaP Cell Line

Before a day, LNCaP cell lines were seed to 24-well plate at a concentration of $1 \times 10^5$ cells/well. When the cells grew uniformly in each plate to be about 60-70%, the culture medium in the plate were removed and then added with new medium at 500 µl/well. 50 µl of culture medium without the fetal bovine serum was poured to eppendorf tube, and were added with 1 µl of Block-iT (20 µmol, Invitrogen, USA) which was siRNA labeled with fluorescent marker, and cationic polymer conjugate 1-50 µl of COMPARATIVE EXAMPLE 1 and EXAMPLE 25, respectively. The solution was mixed with slow pipetting and left at room temperature for 20 minutes. The obtained complex was added to the 24-well plate and cultured in $CO_2$ incubator at 37° C. for 24 hours. The medium of cultured cell was replaced with new medium at 500 µl/well and then observed with fluorescence microscope to analyze the efficiency of delivering a gene.

Figure 11:
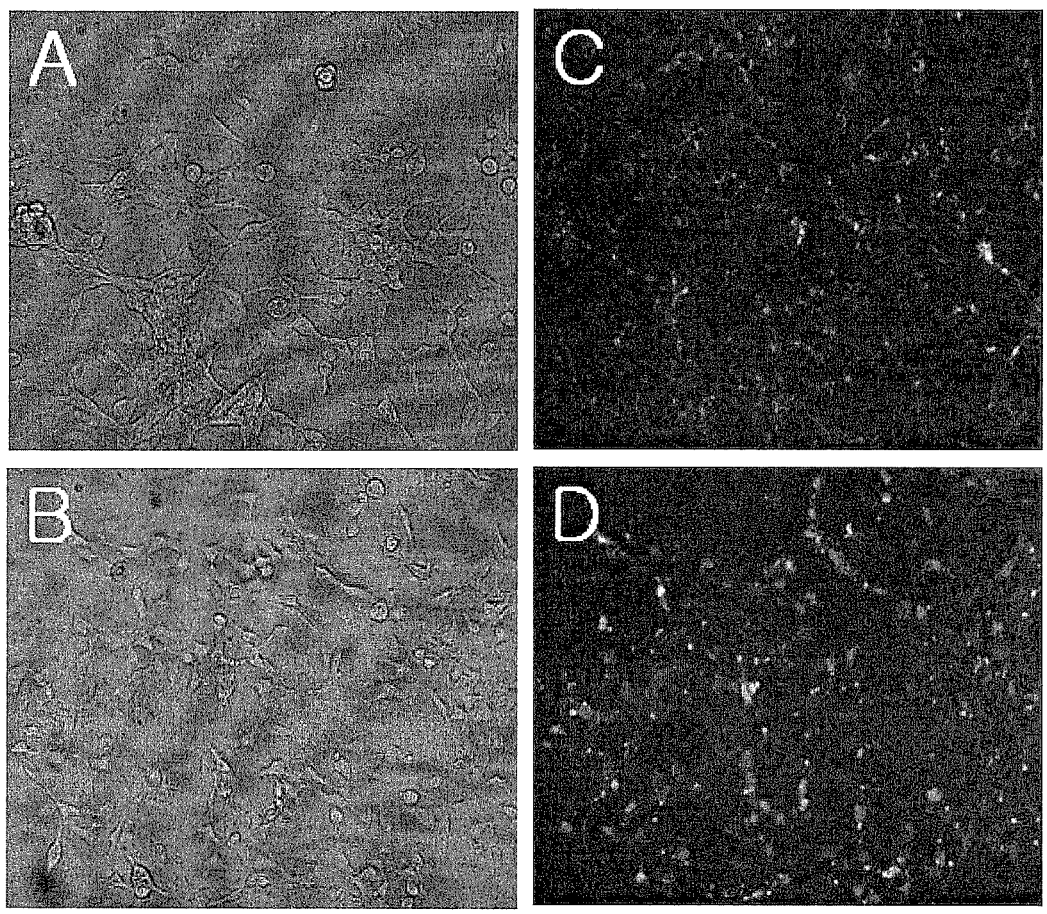
FIG. 11 shows the efficiency of delivering RNA by using cationic polymer conjugates obtained in Example 25 and Comparative Example 1 with confocal microscope and fluorescent microscope.

FIG. 11 shows the delivering efficiency of ribonucleic acid by cationic polymer conjugates obtained in Example 25 and Comparative Example 1 with confocal microscope and fluorescent microscope. Specifically, (A) part of FIG. 11 is a picture of fluorescent microscope obtained by treating with the polymer conjugate of Comparative Example 1 and then analyzed with confocal microscope, and (B) part is a picture of fluorescent microscope obtained by treating with the polymer conjugate of Example 25 and then analyzed with confocal microscope. Part (C) of FIG. 11 is a picture of fluorescent microscope showing the delivery efficiency of siRNA which was treated with the complex of the cationic polymer conjugates obtained Comparative Example 1. Part (D) is a picture of fluorescent microscope showing the delivery efficiency of siRNA which was treated with the complex of the cationic polymer conjugates obtained Example 25. As shown in FIG. 11, HA-PEI conjugate of EXAMPLE 25 delivered siRNA more effectively in LNCaP cell than PEI of Comparative Example 1.

Example 55

Evaluation of Delivery Efficiency of siRNA in Caski Cell Line

Before a day, Caski cell lines were seed to 24-well plate at a concentration of $1 \times 10^5$ cells/well. When the cells grew uniformly in each plate to be about 60-70%, the culture medium in the plate were removed and then added with new medium at 500 µl/well. 50 µl of culture medium without the fetal bovine serum was poured to eppendorf tube, and were added with 1 µl of Block-iT (20 µmol, Invitrogen, USA) which was siRNA labeled with fluorescent marker, and cationic polymer conjugate 1-50 µl of COMPARATIVE EXAMPLE 1 and EXAMPLE 33, respectively. The solution was mixed with slow pipetting and left at room temperature for 20 minutes. The obtained complex was added to the 24-well plate and cultured in $CO_2$ incubator at 37° C. for 24 hours. The medium of cultured cell was replaced with new medium at 500 μl/well and then observed with fluorescence microscope to analyze the efficiency of delivering a gene.

Figure 12:
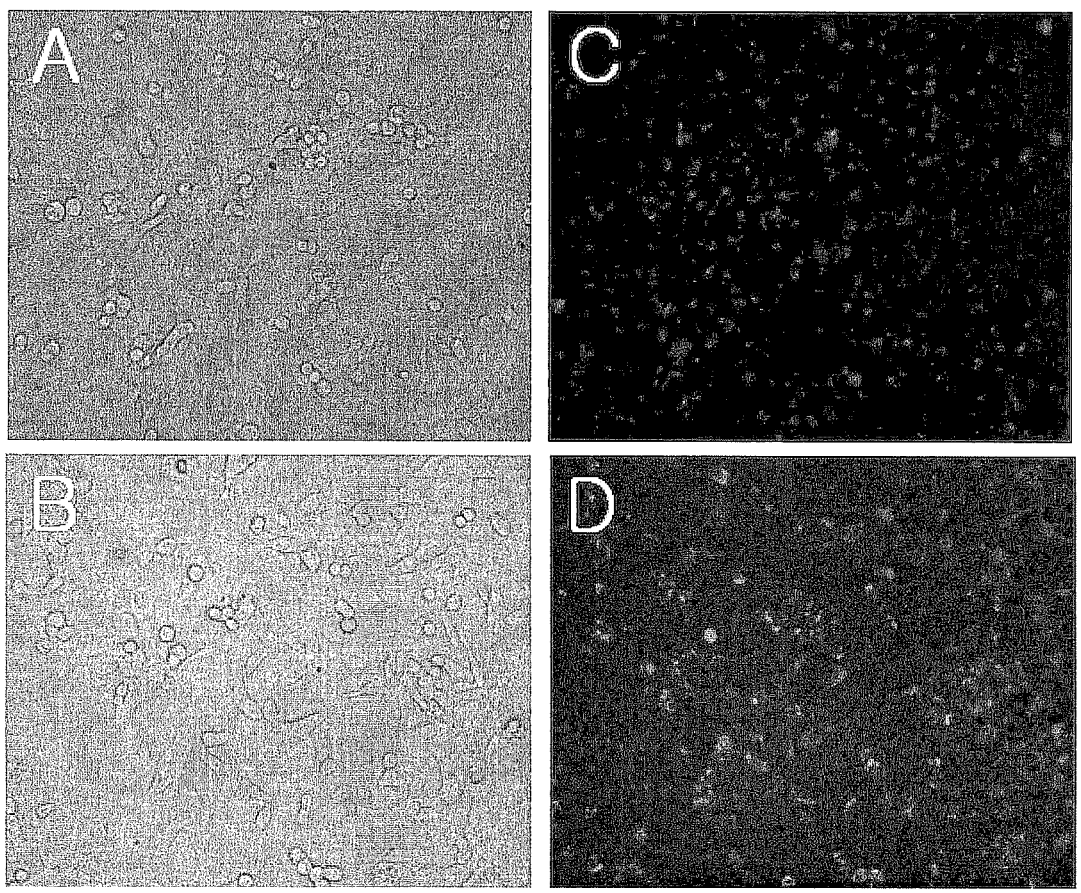
FIG. 12 shows the efficiency of delivering RNA by using cationic polymer conjugates obtained in Example 33 and Comparative Example 1 with confocal microscope and fluorescent microscope.

FIG. 12 shows the delivering efficiency of ribonucleic acid by cationic polymer conjugates obtained in Example 33 and Comparative Example 1 with confocal microscope and fluorescent microscope. Specifically, (A) part of FIG. 12 is a picture of fluorescent microscope obtained by treating with the polymer conjugate of Comparative Example 1 and then analyzing with confocal microscope, and (B) part is a picture of fluorescent microscope obtained by treating with the polymer conjugate of Example 33 and then analyzed with confocal microscope. Part (C) of FIG. 12 is a picture of fluorescent microscope showing the delivery efficiency of siRNA which was treated with the complex of the cationic polymer conjugates obtained Comparative Example 1. Part (D) is a picture of fluorescent microscope showing the delivery efficiency of siRNA which was treated with the complex of the cationic polymer conjugates obtained Example 33. As shown in FIG. 12, HA-PEI conjugate of EXAMPLE 33 delivered siRNA more effectively in Caski cell than PEI of Comparative Example 1.

Example 56

Evaluation of Delivery Efficiency of siRNA in Hep3B Cell Line with Fluorescence Activated Cell Sorting (FACS) Method The efficiency of PEI conjugate to deliver the nucleic acid was evaluated with FACS method.

Before a day, Hep3B cell lines were seed to 12-well plate at a concentration of 2×10⁵ cells/well. When the cells grew uniformly in each plate to be about 60-70%, the culture medium in the plate were removed and then added with new medium at 800 μl/well. 100 μl of culture medium without the fetal bovine serum was poured to eppendorf tube, and were added with 2 μl of Block-iT (20 μmol, Invitrogen, USA) which was siRNA labeled with fluorescent marker, and cationic polymer conjugate 5 μl of COMPARATIVE EXAMPLE 1 and Examples 11 and 37, respectively. The solution was mixed with slow pipetting and left at room temperature for 20 minutes. The obtained complex was added to the 24-well plate and cultured in CO₂ incubator at 37° C. for 24 hours. The medium of cultured cell was replaced with new medium at 500 μl/well and then observed with fluorescence microscope to analyze the efficiency of delivering a gene. The cultured cells were collected and washed twice with phosphate buffer. The washed cells were analyzed with BD FACS CALIBUR (BD Bioscience, USA) and then the delivery efficiency into cell was evaluated by analyzing shift of the fluorescence peak.

Figure 13:
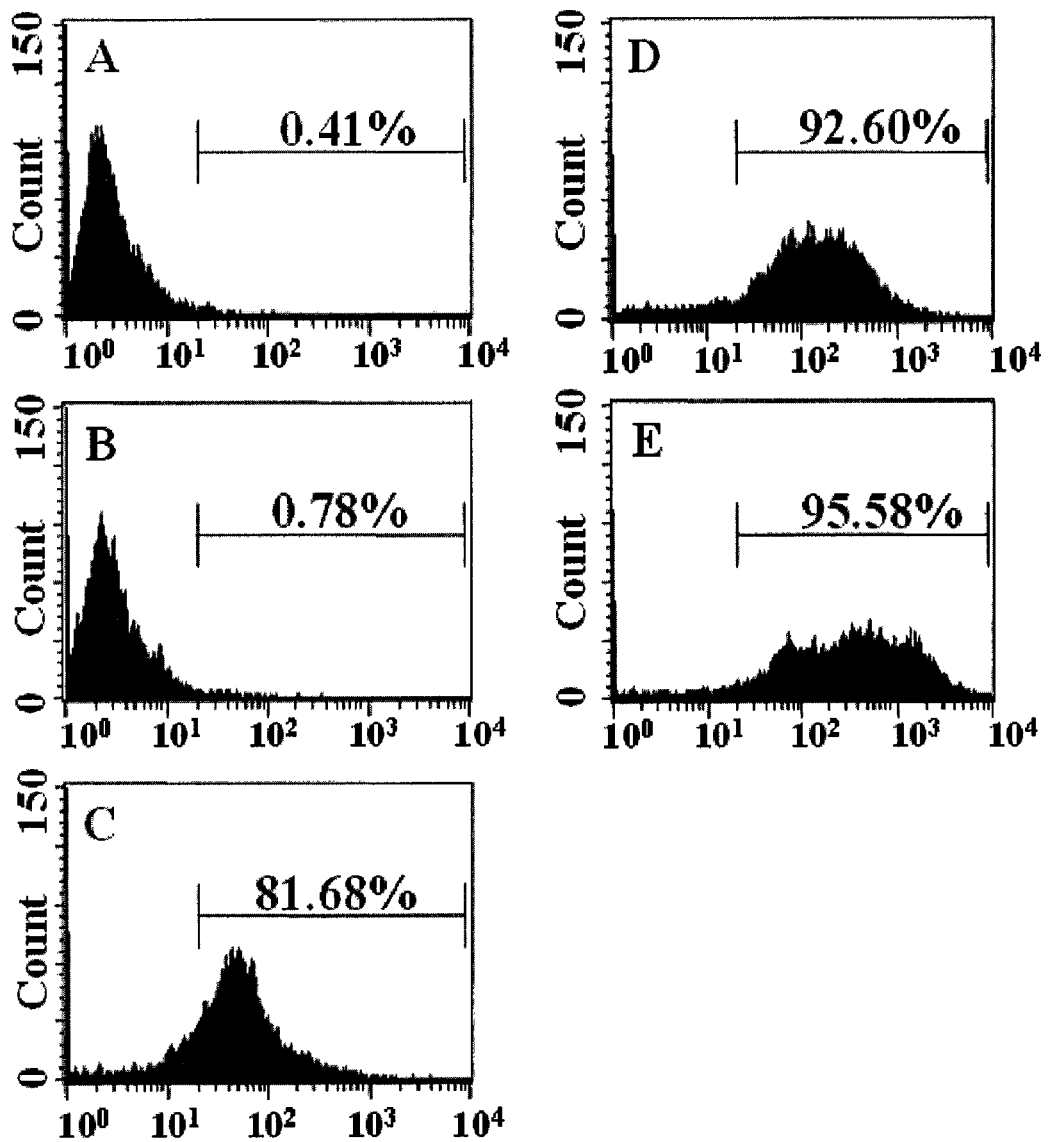
FIG. 13 shows the efficiency of delivering RNA by using cationic polymer conjugates obtained in Example 11 and Example 37 with confocal microscope and fluorescent microscope.

FIG. 13 shows the delivering efficiency of RNA by cationic polymer conjugates obtained in Example 11 and Example 37. In Table 1, the delivery efficiency of ds RNA in each test group was measured quantitatively with FACS analysis. Control group (A) for a group with no treatment of siRNA, test group (B) for treatment of only siRNA without carrier. Control group (A) and test group (B) showed little shift of peak because RNA labeled with fluorescence did not delivered to the cell. Test group (C) was the cell group treated with conventional cationic polymer conjugate obtained from Comparative Example 1, and showed 81.68% of the delivery efficiency of RNA. On the other hand, test group (D) and test group (E) treated with the carrier obtained from Examples 11 and 37 showed the delivery efficiency of 92.60%, and 95.58%, respectively, which increased the delivery efficiency compared test group (C). Accordingly, the results confirmed that the cationic polymer conjugates of Examples 11 and 37 showed increased delivery efficiency of RNA into Hep3B cell lines compared to that of Comparative Example 1.

TABLE 1

Efficiency of delivering siRNA by the cationic polymer conjugate in Hep3B cell line

| Control group (A) | Test group treated with only siRNA (B) | COMPARATIVE EXAMPLE 1 (C) | EXAMPLE 11 (D) | EXAMPLE 37 (E) |
| --- | --- | --- | --- | --- |
| 0.41% | 0.78% | 81.68% | 92.60% | 95.58% |

Example 57

Evaluation of Delivery Efficiency of siRNA in A549 Cell with RT-PCR

Before a day, A549 cell lines were seed to 24-well plate at a concentration of 1×10⁵ cells/well. When the cells grew uniformly in each plate to be about 60-70%, the culture medium in the plate were removed and then added with new medium at 250 μl/well. 25 μl of culture medium without the fetal bovine serum was poured to eppendorf tube, and were added with dsRNA targeting to survivin and 5 μl of cationic polymer conjugates of Comparative Examples 1 and 2, and Example 8, respectively.

To induce the inhibition of gene expression of Survivin gene (Gene bank accession number: NM_001168), dsRNA targeting to surviving was prepared by using siGENOME SMARTpool (Dahrmacon, Lafayette, Colo., USA). The final concentration of dsRNA targeting to surviving was adjusted to 100 nM, and mixed by pipetting, and lett at room temperature for 20 minutes. The obtained complex was added to the 24-well plate and cultured in CO₂ incubator at 37° C. for 24 hours. After 24 hours, whole RNA in cell was separated from by using Trizol reagent (Invitrogen, Carlsbad, Calif., USA), and performed by RT-PCT with AccuPower RT PreMix (Bioneer, Daejeon, Korea). The survivin-specific primers were 5'-GGACCACCG CATCTCTACAT-3'(left) (SEQ ID NO: 1), 5'-CTTTCTCCGCAGTTTCCTCA-3(right) (SEQ ID NO: 2) and the amplified product was 347 base pairs. The expression degree of surviving gene was measured quantitatively by compensating the band density of surviving-specific PCR product with that of glyceraldehyde-3-phosphate dehydrogenase (GAPDH).

Figure 14:
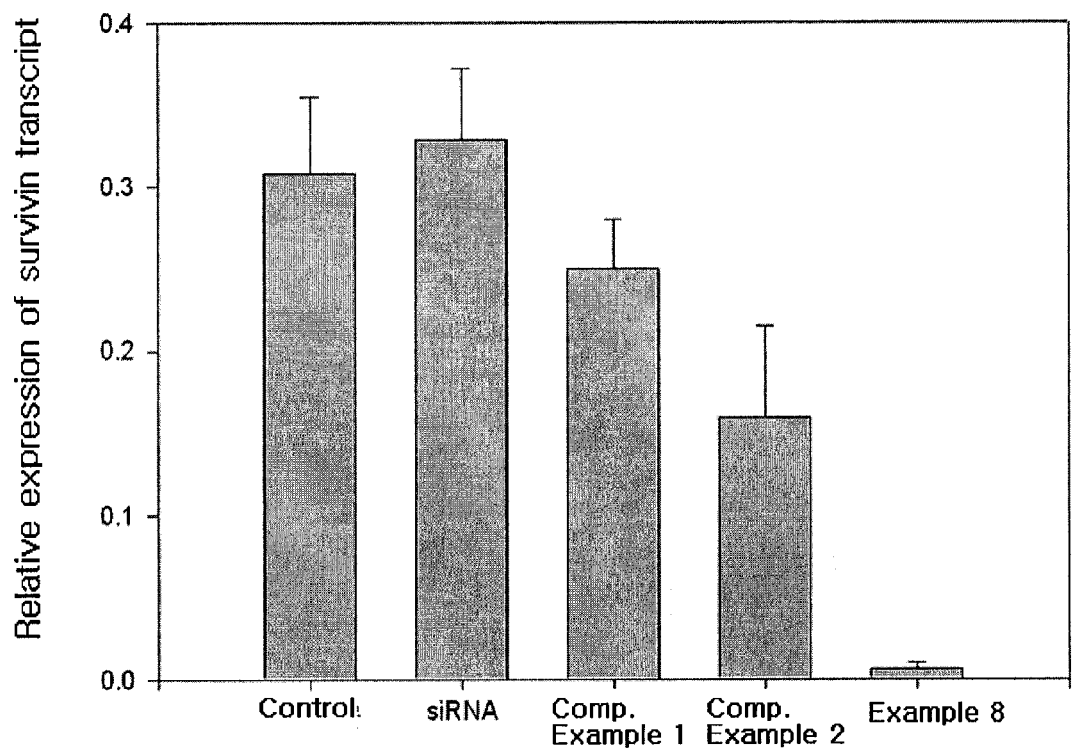
FIG. 14 shows comparison of expression of survivin in A549 cell, when various delivery systems were applied for dsRNA targeting the survivin.

FIG. 14 shows comparison of transcription of survivin in A549 cell when various delivery systems were applied for dsRNA targeting the survivin. No change in expression degree of survivin were in control group and test group (B) treated with only siRNA, which siRNA in the control group and test group were not delivered to the cell. On the other hand, compared to cationic polymer conjugates of Comparative Examples 1 and 2, the cationic polymer conjugate of Example 8 reduce notably the expression of survivin transcript. As shown in FIG. 14, the cationic polymer conjugate obtained from Example 8 delivered effectively siRNA into A549 cell line and thus inhibited effectively the expression of the target gene.

Example 58

Evaluation of Delivery Efficiency of siRNA in HeLa Cell with RT-PCR

Before a day, HeLa cell lines were seed to 24-well plate at a concentration of 1×10⁵ cells/well. When the cells grew uniformly in each plate to be about 60-70%, the culture medium in the plate were removed and then added with new medium at 250 μl/well. Then, the experiment was carried out according to the substantially same method of Example 57.

Figure 15:
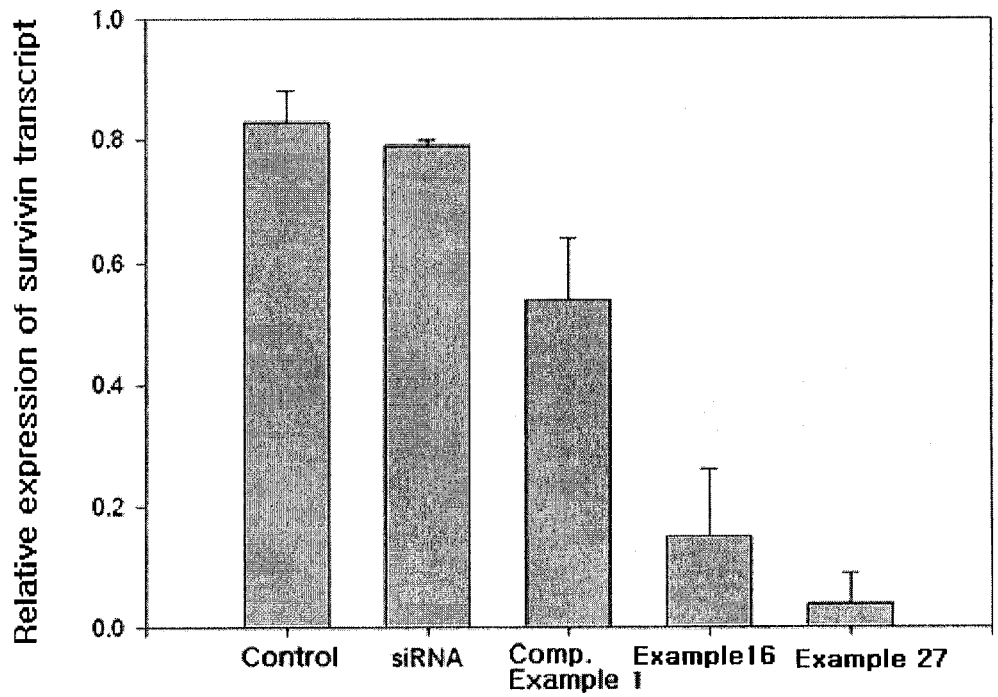
FIG. 15 shows comparison of expression of survivin in HeLa cell, when various delivery systems were applied for dsRNA targeting the survivin.

FIG. 15 shows comparison of transcription of survivin in HeLa cell, when various delivery systems were applied for dsRNA targeting the survivin. No change in expression degree of surviving were in control group and test group (B) treated with only siRNA, which siRNA in the control group and test group were not delivered to the cell. On the other hand, compared to the cationic polymer conjugates of Comparative Example 1, the cationic polymer conjugates of Examples 16 and 27 reduce notably the expression of survivin transcript. As shown in FIG. 15, the cationic polymer conjugate obtained from Examples 16 and 27 delivered effectively siRNA into HeLa cell line and thus inhibited the expression of the target gene effectively.

Example 59

Evaluation of Delivery Efficiency of siRNA in B16F1 Cell with RT-PCR

Before a day, B16F1 cell lines were seed to 24-well plate at a concentration of $1\times10^5$ cells/well. When the cells grew uniformly in each plate to be about 60-70%, the culture medium in the plate were removed and then added with new medium at 250 μl/well. Then, the experiment was carried out according to the substantially same method of Example 57.

Figure 16:
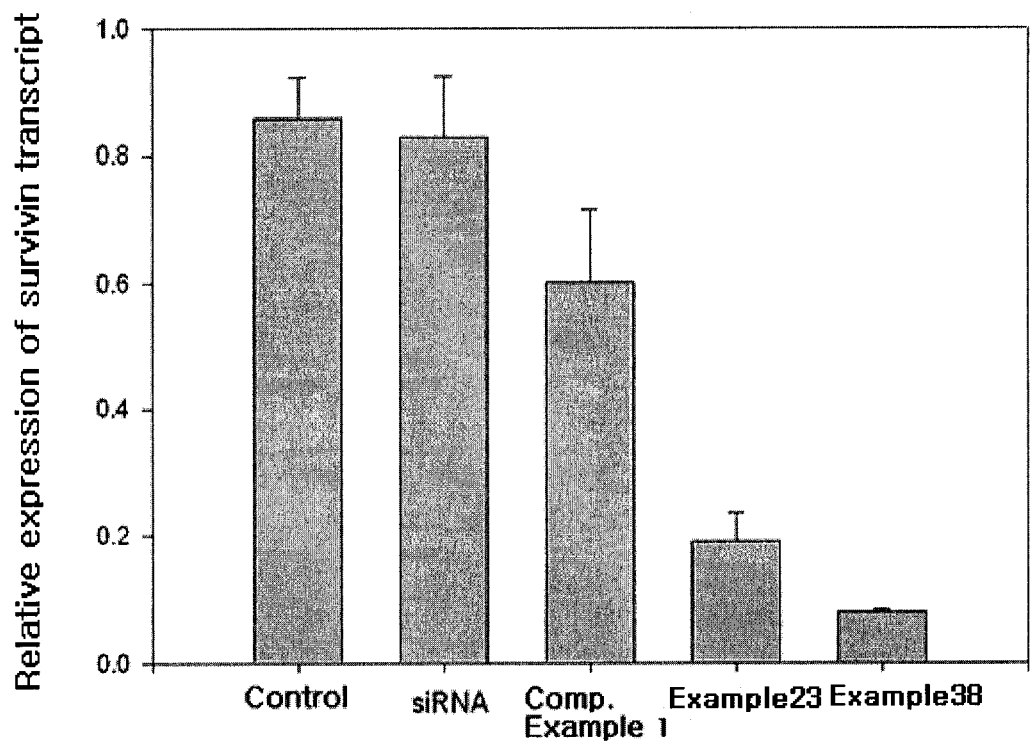
FIG. 16 shows comparison of expression of survivin in B16F1 cell, when various delivery systems were applied for dsRNA targeting the survivin.

FIG. 16 shows comparison of transcription of survivin in HeLa cell, when various delivery systems were applied for dsRNA targeting the survivin. No change in expression degree of surviving were in control group and test group (B) treated with only siRNA, which siRNA in the control group and test group were not delivered to the cell. On the other hand, compared to cationic polymer conjugates of Comparative Example 1, the cationic polymer conjugates of Examples 23 and 38 reduce notably the expression of survivin transcript. As shown in FIG. 16, the cationic polymer conjugate obtained from Examples 23 and 38 delivered effectively siRNA into HeLa cell line and thus inhibited effectively the expression of the target gene.

Example 60

Evaluation of Delivery Efficiency of siRNA in Hep3B Cell with RT-PCR

Before a day, Hep3B cell lines were seed to 24-well plate at a concentration of $1\times10^5$ cells/well. When the cells grew uniformly in each plate to be about 60-70%, the culture medium in the plate were removed and then added with new medium at 250 μl/well. Then, the experiment was carried out according to the substantially same method of Example 57.

Figure 17:
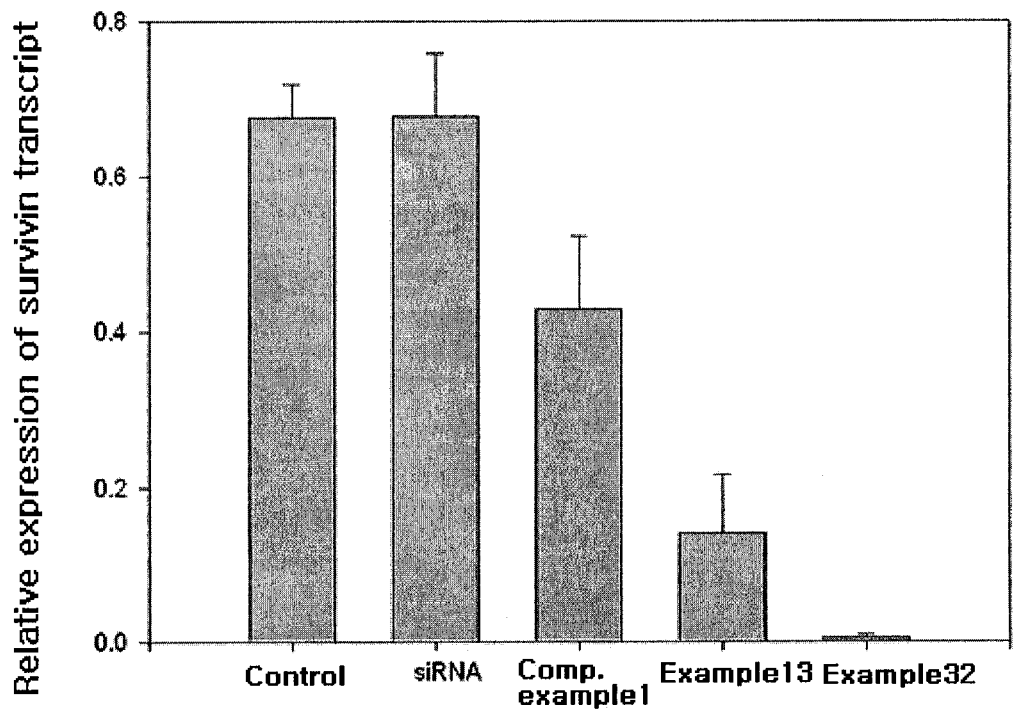
FIG. 17 shows comparison of expression of survivin in Hep3B cell, when various delivery systems were applied for dsRNA targeting the survivin.

FIG. 17 shows comparison of transcription of survivin in HeLa cell, when various delivery systems were applied for dsRNA targeting the survivin. No change in expression degree of surviving were in control group and test group (B) treated with only siRNA, which siRNA in the control group and test group were not delivered to the cell. On the other hand, compared to cationic polymer conjugates of Comparative Example 1, the cationic polymer conjugates of Examples 13 and 32 reduce notably the expression of survivin transcript. As shown in FIG. 17, the cationic polymer conjugate obtained from Examples 13 and 32 delivered effectively siRNA into HeLa cell line and thus inhibited effectively the expression of the target gene.

Example 61

Cytotoxicity Test of the Delivery System in Lung Cancer Cell Line

The cytotoxicity of the cationic polymer conjugate of hyaluronic acid and PEI was evaluated as follows. The human lung cancer cell line, A549 were with no treatment (control group), only scrambled siRNA (siRNA treatment group), a complex including scrambled siRNA and cationic polymer obtained from Comparative Example 1, a complex including scrambled siRNA and commercially-available cationic polymer of Comparative Example 2, and a complex including obtained from Examples 4 and 15. The cytotoxicity was performed with MTT (3-(4,5-dimethylthiazole-2-yl)-2,5-diphenyl tetrazolium bromide). Cell lines were seed to 48-well plate at a concentration of $5\times10^4$ cells/well, cultured for 12 hours and added with a complex of siRNA and 1 μl of commercially-available cationic liposome of Comparative Example 2, a complex of siRNA and each 5 μl of Comparative Example 1 and Examples 4 and 15, and only scrambled siRNA. After 24 hours, the cell was added with MTT solution at an amount of 10% of medium amount, cultured for 4 hours, removed from the supernatant, added with 0.06N HCl and isopropanol solution and the absorbance at 570 nm was read with ELISA reader.

Figure 18:
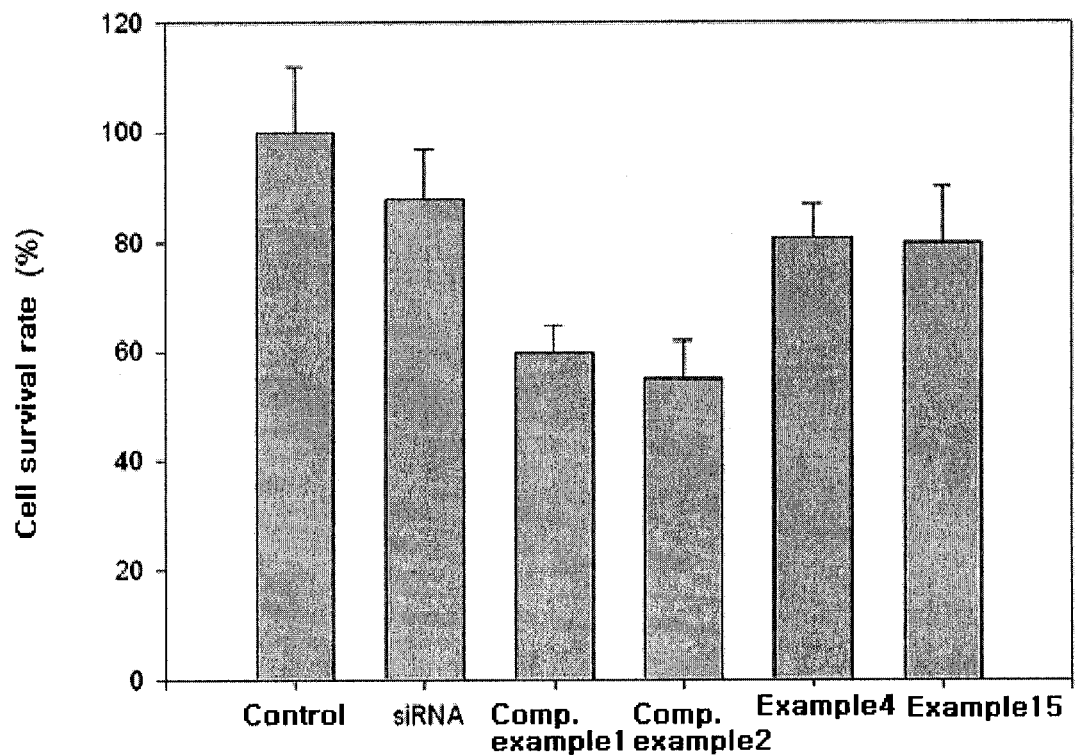
FIG. 18 shows cytotoxicity test results of complexes including cationic polymer conjugates obtained in Examples 4 and 15, and Comparative Examples 1 and 2 in A549 cell as a lung cancer cell line.

FIG. 18 shows cytotoxicity test results of complexes including cationic polymer conjugates obtained in Examples 4 and 15, and Comparative Examples 1 and 2 in A549 cell as a lung cancer cell line.

The complex of siRNA and cationic polymer obtained Comparative Example 1 showed a control group. On the other hand, the complexes of siRNA and cationic polymer conjugates obtained from Examples 4 and 15 had low cytotoxicity. Accordingly, the cationic polymer conjugates of Examples 4 and 15 was smaller cytotoxicity in lung cancer cell line than cationic polymer and cationic liposome of Comparative Examples 1 and 2.

Example 62

Cytotoxicity Test of the Delivery System in Cervical Cancer Cell Line

The cytotoxicity of the cationic polymer conjugate of hyaluronic acid and PEI was evaluated as follows. The human cervical cancer cell line, HeLa were with no treatment (control group), only scrambled siRNA (siRNA treatment group), a complex including scrambled siRNA and cationic polymer obtained from Comparative Example 1, a complex including scrambled siRNA and commercially-available cationic polymer of Comparative Example 2, and a complex including obtained from Examples 21 and 33. The cytotoxicity was performed with MTT (3-(4,5-dimethylthiazole-2-yl)-2,5-diphenyl tetrazolium bromide). Cell lines were seed to 48-well plate at a concentration of $5\times10^4$ cells/well, cultured for 12 hours and added with a complex of siRNA and 1 μl of commercially-available cationic liposome of Comparative Example 2, a complex of siRNA and each 5 μl of Comparative Example 1 and Examples 21 and 33, and only scrambled siRNA. After 24 hours, the cell was added with MTT solution at an amount of 10% of medium amount, cultured for 4 hours, removed from the supernatant, added with 0.06N HCl and isopropanol solution, and the absorbance at 570 nm was measured with ELISA reader.

Figure 19:
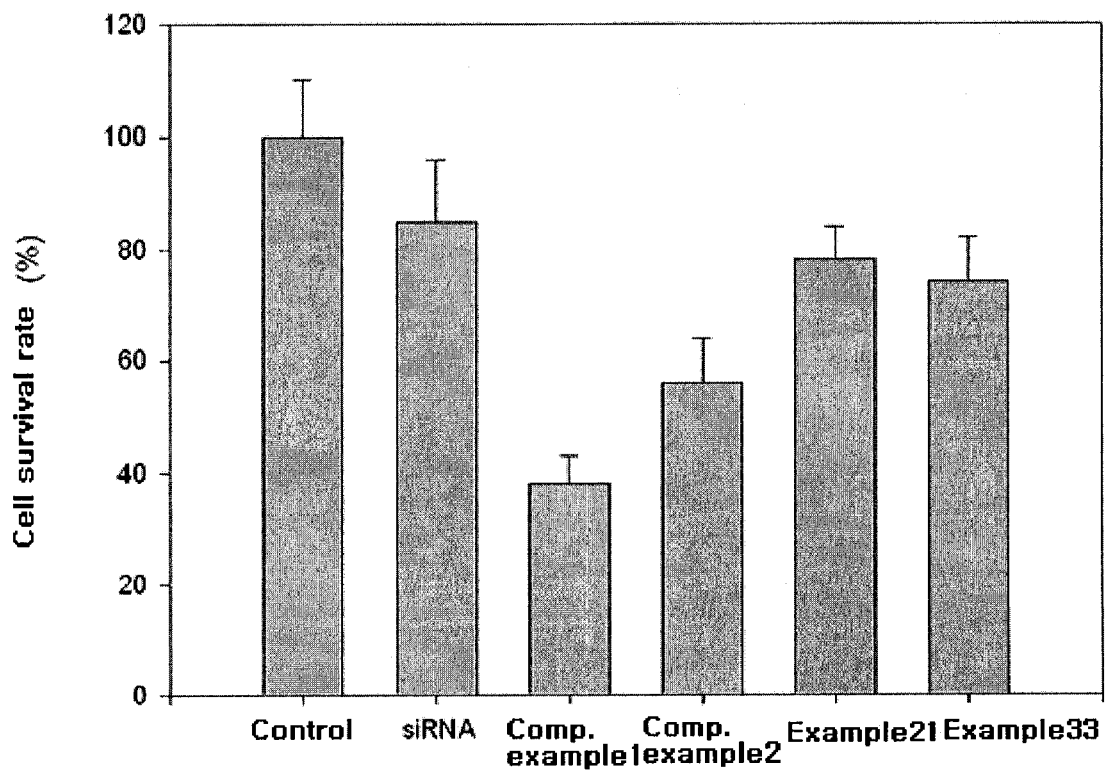
FIG. 19 shows cytotoxicity test results of complexes including cationic polymer conjugates obtained in Examples 21 and 33, and Comparative Examples 1 and 2 in HeLa cell as a human cervical cancer cell line.

FIG. 19 shows cytotoxicity test results of complexes including cationic polymer conjugates obtained in Examples 21 and 33, and Comparative Examples 1 and 2 in A549 cell as a cervical cancer cell line. The complex of siRNA and cationic polymer obtained Comparative Example 1 showed a control group. On the other hand, the complexes of siRNA and cationic polymer conjugates obtained from Examples 21 and 33 had low cytotoxicity. Accordingly, the cationic polymer conjugates of Examples 21 and 33 was smaller cytotoxicity in cervical cancer cell line than cationic polymer and cationic liposome of Comparative Examples 1 and 2.

Example 63

Cytotoxicity Test of the Delivery System in Melanoma Cell Line

The cytotoxicity of the cationic polymer conjugate of hyaluronic acid and PEI was evaluated as follows. The melanoma cell line, B16F1 were with no treatment (control group), only scrambled siRNA (siRNA treatment group), a complex including scrambled siRNA and cationic polymer obtained from Comparative Example 1, a complex including scrambled siRNA and commercially-available cationic polymer of Comparative Example 2, and a complex including obtained from Examples 21 and 33. The cytotoxicity was performed with MTT (3-(4,5-dimethylthiazole-2-yl)-2,5-diphenyl tetrazolium bromide). Cell lines were seed to 48-well plate at a concentration of $5 \times 10^4$ cells/well, cultured for 12 hours and added with a complex of siRNA and 1 µl of commercially-available cationic liposome of Comparative Example 2, a complex of siRNA and each 5 µl of Comparative Example 1 and Examples 17 and 38, and only scrambled siRNA. After 24 hours, the cell was added with MTT solution at an amount of 10% of medium amount, cultured for 4 hours, removed from the supernatant, added with 0.06N HCl and isopropanol solution, and the absorbance at 570 nm was read with ELISA reader.

Figure 20:
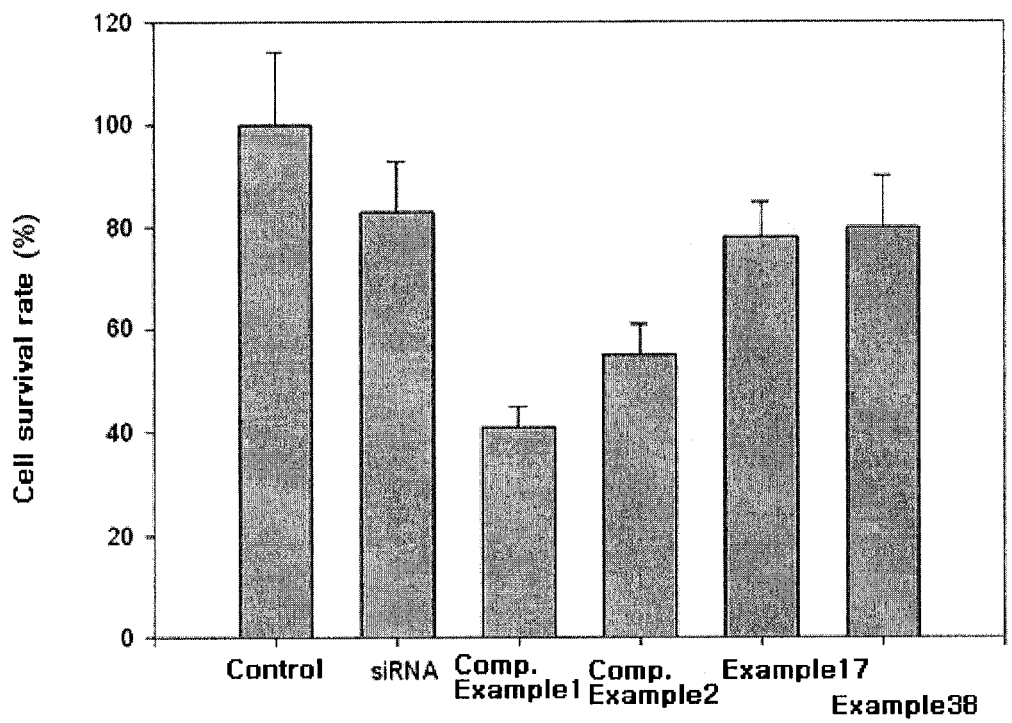
FIG. 20 shows cytotoxicity test results of complexes including cationic polymer conjugates obtained in Examples 17 and 38, and Comparative Examples 1 and 2 in B16F1 cell as a melanoma cell line

FIG. 20 shows cytotoxicity test results of complexes including cationic polymer conjugates obtained in Examples 17 and 38, and Comparative Examples 1 and 2 in A549 cell as a melanoma cell line. The complex of siRNA and cationic polymer obtained Comparative Example 1 showed a control group. On the other hand, the complexes of siRNA and cationic polymer conjugates obtained from Examples 17 and 38 had low cytotoxicity. Accordingly, the cationic polymer conjugates of Examples 17 and 38 was smaller cytotoxicity in melanoma cell line than cationic polymer and cationic liposome of Comparative Examples 1 and 2.

Example 64

Evaluation of Cell Damage in Lung Cancer Cell Line

The cell damage of the cationic polymer conjugate of hyaluronic acid and PEI was evaluated as follows. The lung cancer cell line, A549 were with no treatment (control group), only scrambled siRNA (siRNA treatment group), a complex including scrambled siRNA and cationic polymer obtained from Comparative Example 1, a complex including scrambled siRNA and commercially-available cationic polymer of Comparative Example 2, and a complex including obtained from Examples 5 and 19 to evaluate the cell damage. The cell damage was measured with TAKARA LDH cell damage detecting kit which detected lactate dehydrogenase (LDH) at high sensitivity. The cell lines were seed to 48-well plate at a concentration of $5 \times 10^4$ cell/well, and cultured for 12 hours, and added with a complex including 1 µl of commercially-available cationic liposome of Comparative Example 2 and siRNA, a complex including 5 µl of each cationic polymer conjugate obtained from Examples 5 and 19 and siRNA, and only siRNA. After 16 hours, the culture medium was replaced with new medium not including fetal bovine serum. The control group was added with Triton X-100 to a concentration of 3% to detect the maximum LDH activity. After culturing for more 8 hours, the tissue culture plate was centrifuged at 250×g rpm for 10 minutes, and 100 µl/well of the supernatant was taken and transferred to transparent 96-well plate, and then added with 100 µl of a mixture of solution A (diaphalose/NAD+ddH$_2$O) and solution B (INT/Na-lactate). Under no light condition, the plate was left at room temperature for 30 minutes, and the absorbance at 492 nm was read with ELISA reader.

Figure 21:
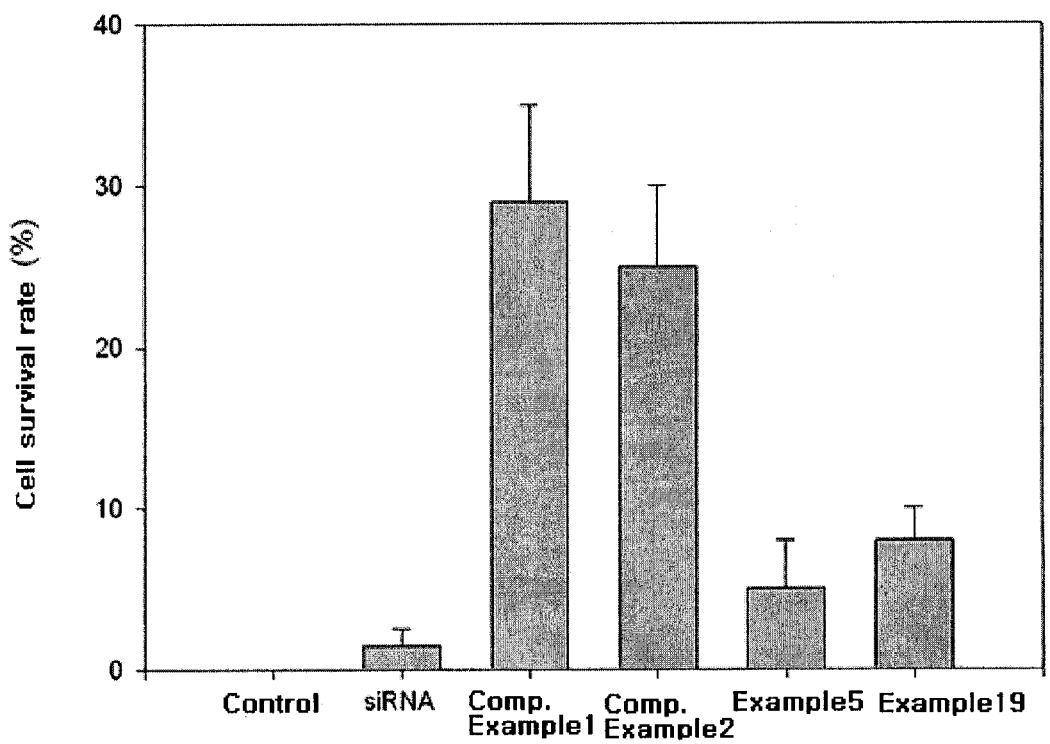
FIG. 21 shows cell damage test result in A549 cell with the complexes including cationic polymer conjugates obtained in Examples 5 and 19 and Comparative Example 1 and scrambled siRNA, and the complex including cationic phospholipid liposome of Comparative Example 2 and scrambled siRNA.

FIG. 21 shows cell damage test result in A549 cell with a complex including scrambled siRNA and 5 µl of each cationic polymer conjugates obtained in Examples 5 and 19, and a complex including siRNA and Comparative Example 1 and scrambled siRNA, and 1 µl of cationic phospholipid liposome of Comparative Example 2 and scrambled siRNA. The complexes including scrambled siRNA and cationic polymer of Comparative Example 1 or cationic liposome of Comparative Example 2 showed large cell damage. On the other hand, the complexes including scrambled siRNA and cationic polymer conjugates of Examples 5 and 19 showed notably-reduced cell damage. Thus, the result suggested that the cationic polymer conjugates obtained from Examples 5 and 19 had lower cell damage in lung cancer cell line than cationic polymer of Comparative Example 1 and cationic liposome of Comparative Example 2.

Example 65

Evaluation of Delivery Efficiency of Antisense Oligonucleic Acid in Lung Cancer Cell To evaluate a cationic polymer conjugate of hyaluronic acid and PEI to deliver the antisense oligonucleic acid, an antisense oligonucleic acid targeting Bcl-2, a gene inhibiting cell apoptosis was used. The lung cancer cell line, A549 were with no treatment (control group), only Bcl-2-specific antisense oligonucleic acid (G3139), a complex including G3139 and the cationic polymer obtained from Comparative Example 1, a complex including G3139 and commercially-available cationic polymer of Comparative Example 2, and a complex including G3139 and cationic polymer conjugates obtained from Examples 11 and 34 and then measured with the expression amount of Bcl-2 transcript to the delivering extent of antisense oligonucleic acid into A549 cell.

Before a day, A549 cell lines were seed to 24-well plate at a concentration of $1 \times 10^5$ cells/well. When the cells grew uniformly in each plate to be about 60-70%, the culture medium in the plate were removed and then added with new medium at 250 µl/well. 25 µl of culture medium without the fetal bovine serum was poured to eppendorf tube, and were mixed by pipetting with addition of G3139 and 5 µl of cationic polymer of Comparative Example 2, and carriers of Examples 11 and 34, and left at room temperature for 20 minutes. The obtained complex was added to the 24-well plate and cultured in $CO_2$ incubator at 37° C. for 24 hours.

After 24 hours, whole RNA in cell was separated by using Trizol reagent (Invitrogen, Carlsbad, Calif., USA), and performed by RT-PCT with AccuPower RT PreMix (Bioneer, Daejeon, Korea) to produce cDNA. The primers specific to Bcl-2 are 5'-ATG GCG CAC GCT GGG AGA AC-3'(left) (SEQ ID NO: 3), and 5'-GCG GTA GCG GCG GGA GAA GT-3'(right) (SEQ ID NO: 4), and the amplified product was 327 base pairs. The expression degree of Bcl-2 transcript was measured quantitatively by compensating the band density of Bcl-2-specific PCR product with that of glyceraldehyde-3-phosphate dehydrogenase (GAPDH).

Figure 22:
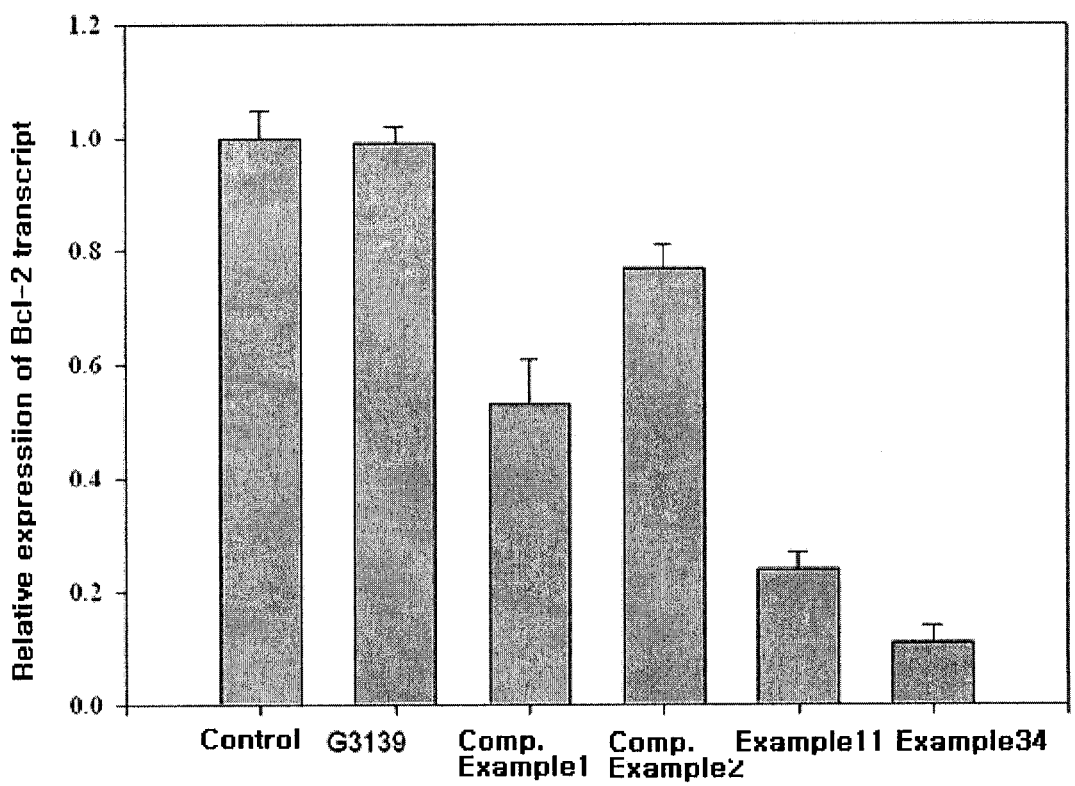
FIG. 22 shows comparison of the expression of transcript Bcl-2 by delivering with complexes of cationic polymer conjugates obtained in Examples 11 and 34 and Bcl-2-selective G3139 antisense oligonucleic acid.

FIG. 22 shows comparison the expression of transcript Bcl-2 by delivering with complexes of cationic polymer conjugates obtained in Examples 11 and 34 and Bcl-2 selective G3139 antisense oligonucleic acid. The test group treated with only G3139 showed no different expression degree of Bcl-2 compared to the control group. On the other hand, when the Bcl-2 was delivered with the carriers of Comparative Examples 1 and 2, the expression degree of Bcl-2 was reduced. When the Bcl-2 was delivered with the cationic polymer conjugates obtained from Examples 11 and 34, the expression degree of Bcl-2 transcript were reduced relatively at a maximum value. Accordingly, the result showed that the cationic polymer conjugates of Examples 11 and 34 had a capacity of delivering the antisense oligonucleic acid into the cell lines.

Example 66 siRNA/PEI-HA Toxicity Test and Report Gene Test

Figure 23:
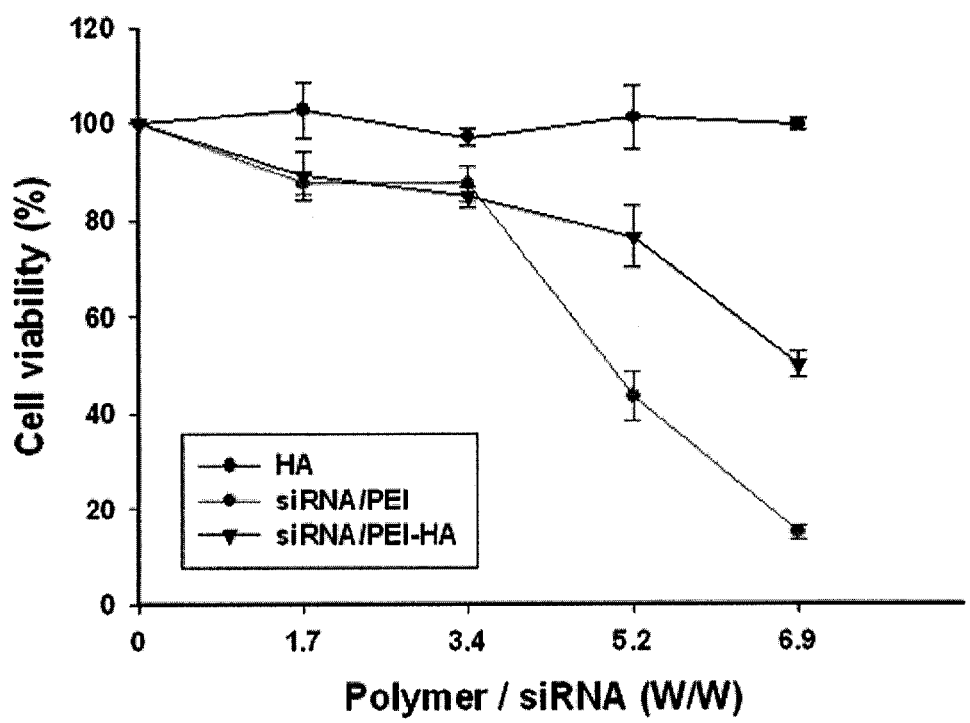
FIG. 23 shows the survival rate in B16F1 compared to HA and PEI as a control, as the weight ratio of HA-PEI to siRNA increased.

To evaluate the complex, in case that the ratios of HA-PEI to siRNA in the complex were various, the cell survival rate was measured with MTT assay (see FIG. 23). FIG. 23 shows the survival rate in B16F1 as the ratio of HA-PEI to siRNA increased with HA and PEI as a control.

Figure 24:
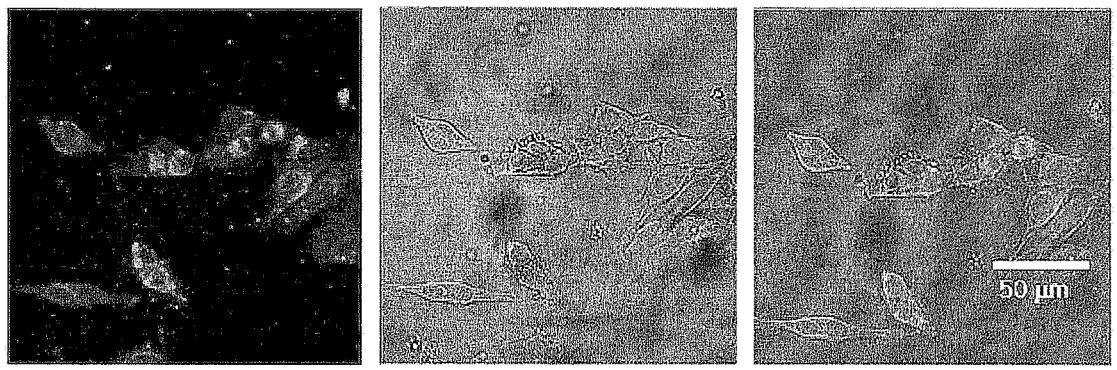
FIG. 24 shows confocal microscopy result of siRNA labeled with FITC and HA-PEI conjugate in B16F1 cell (A) and HEK-293 cell (B).
Figure 24:
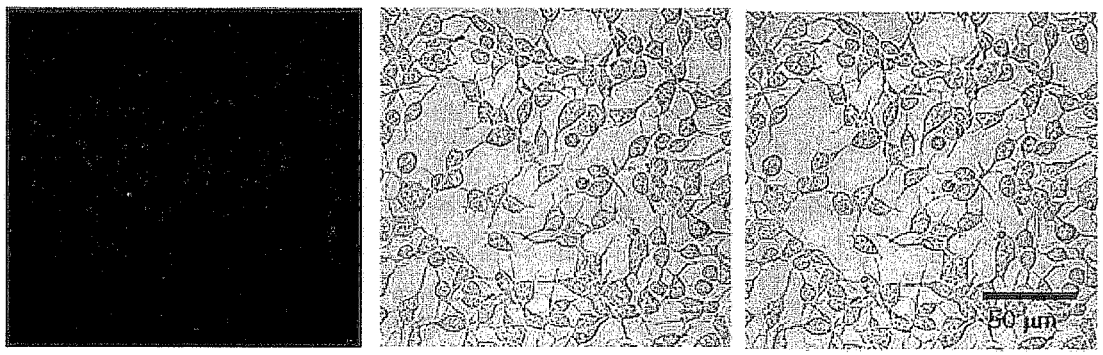

In order that the HA-PEI conjugate has delivering capacity specific to the cancer cell, siRNA/HA-PEI complex was labeled with FIT, and the delivery efficiency was compared in both B16F1 cell with overexpression of the HA receptor LYVE-1 and HEK-293 without LYVE-1. Specifically, B16F1 cell and HEK-293 cell were cultured in 10% fetal bovine serum and 100 U/mL penicillin-streptomycin enriched DMEM medium (GIBCO-BRL, NY, USA), seed to 24-well plate, respectively, and cultured at 37° C. and 5% $CO_2$ atmosphere to be about 60-70% of cell density. Then, FITC-siRNA/HA-PEI complex was added to each well, cultured for 2 hour, fixed and then observed with confocal laser microscope to show the result in FIG. 24. FIG. 24 is confocal microscopy result of siRNA labeled with FITC and HA-PEI conjugate in B16F1 cell (A) and HEK-293 cell (B).

Figure 25A:
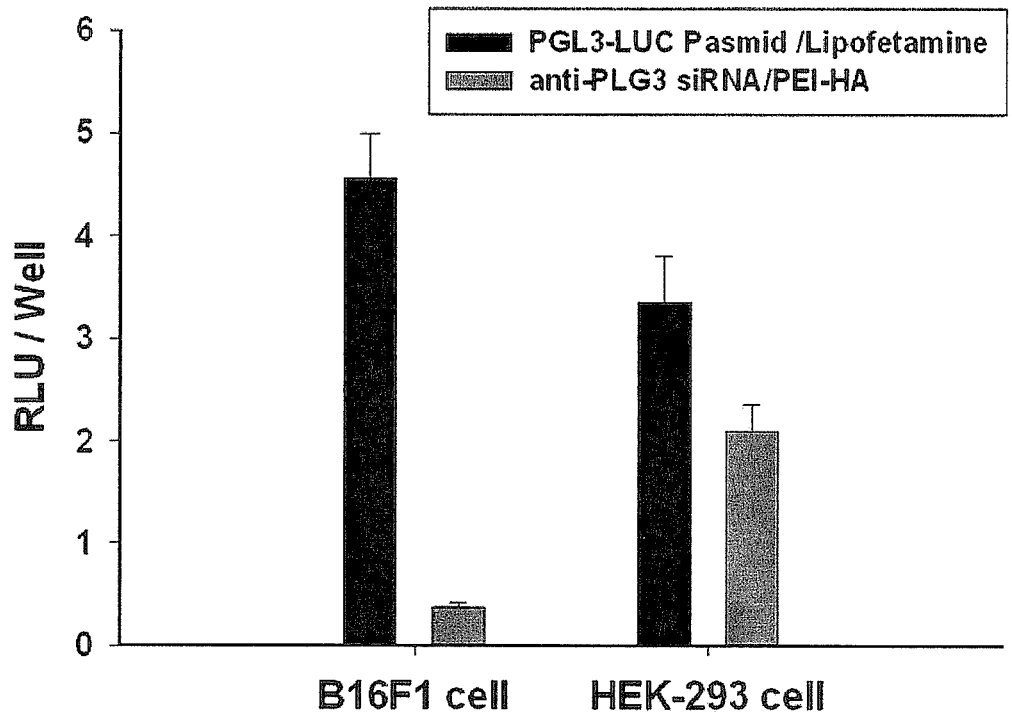
FIGS. 25A and 25B show the inhibition of anti-PGL3-Luc siRNA/HA-PEI complex on the expression of Luciferase protein measured by using a reporter gene of PGL3-Luc in B16F1 cell and HEK-293 cell; (A) absolute light intensity and (B) the comparison of standardized inhibition degree. The inhibition of Luciferase expression was larger in B16F1 cell including the receptor of hyaluronic acid than in HEK-293 cell.
Figure 25B:
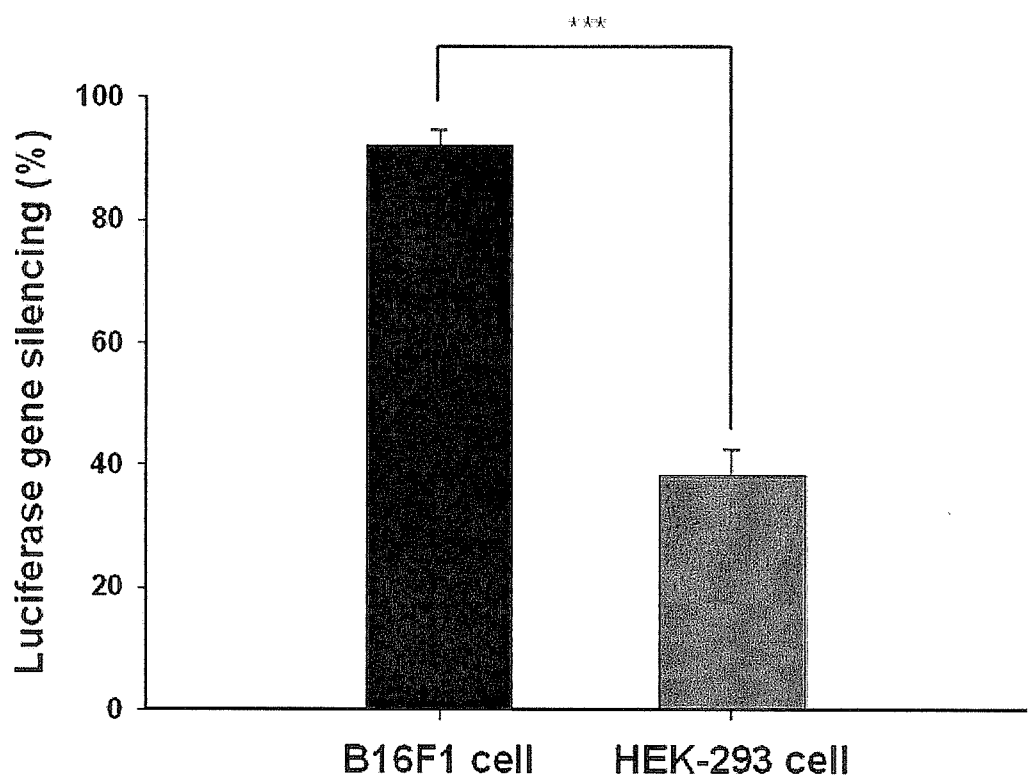

To measure the gene silencing of siRNA by using reporter gene, Luciferase, the gene splicing of HA-PEI/Anti-PGL3-Luc siRNA complex was carried out. The cells on 24-well plate were cultured with addition of Lipofectamine/PGL3-Luc complex for 3 hours, washed, cultured with addition of HA-PEI/Anti-PGL3-Luc siRNA complex for 30 minutes and the Luciferase activity was detected with Luminometer (Lumat, LB 9501, Berthold, Germany) for 30 seconds to show the results in FIGS. 25A and 25B. FIGS. 25A and 25B show the inhibition of anti-PGL3-Luc siRNA/HA-PEI complex on the expression of Luciferase protein measured by using a reporter gene of PGL3-Luc in B16F1 cell and HEK-293 cell; (A) absolute light intensity and (B) the comparison of standardized inhibition extent. The inhibition of Luciferase expression was larger in B16F1 cell where the receptor of hyaluronic acid are located than in HEK-293 cell.

Figure 26:
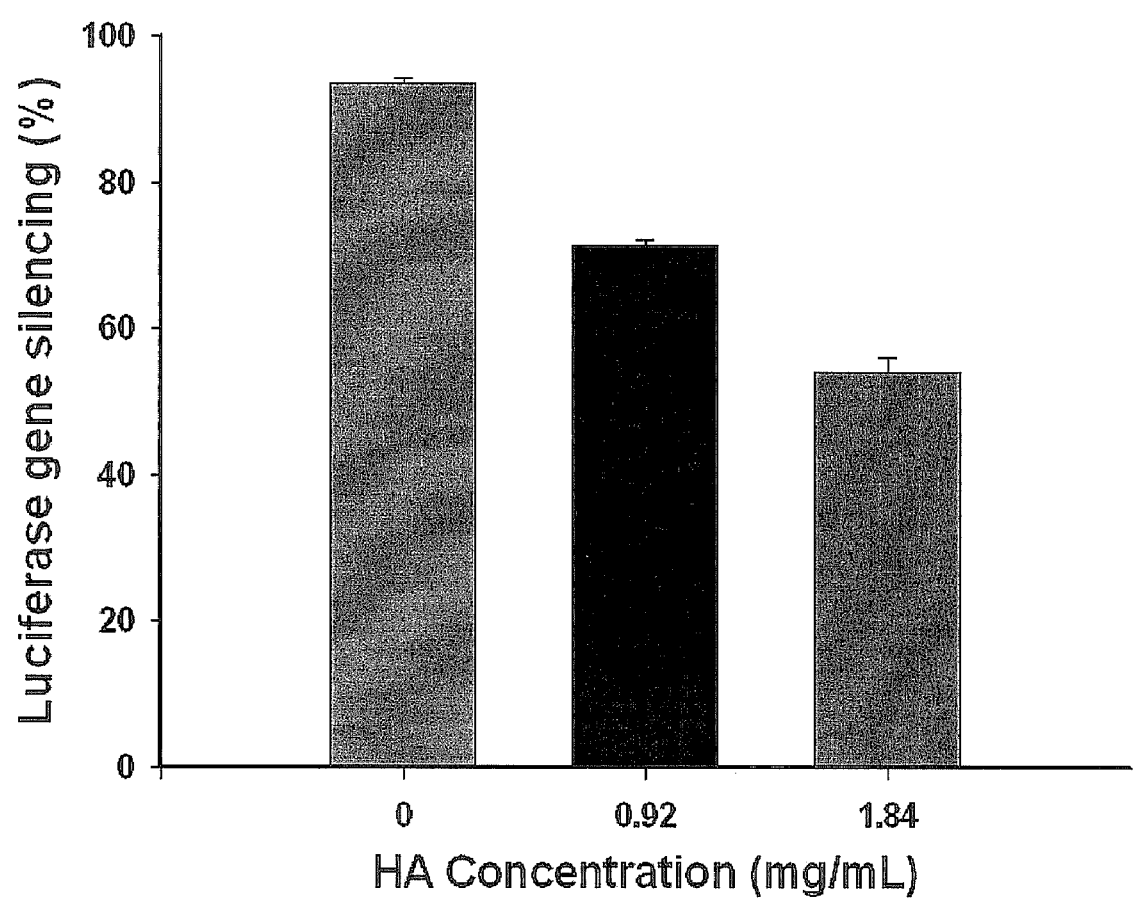
FIG. 26 shows the reduced inhibition efficiency of Luciferase expression, as the concentration of hyaluronic acid in medium increased.

To observe the receptor-specific endocytosis, as the concentration of HA in medium was various, the gene silencing effect was observed to show FIG. 26. As the concentration of HA increased, it inhibited the endocytosis of HA-PEI/Anti-PGL3-Luc siRNA complex by binding to the receptor on cell surface. FIG. 26 shows the decrease of inhibition of Luciferase expression as the concentration of hyaluronic acid in medium increased Luciferase. As the concentration of HA increased, the inhibition of protein expression was decreased.

Example 67

Anti-Cancer Activity of HA-PEI/VGEF Specific siRNA Complex

To evaluate the anti-cancer activity of HA-PEI/VEGF specific siRNA complex, $1 \times 10^6$ of B16F1 melanoma cancer cell were injected subcutaneously into mouse' left armpit to produce cancer model, and then short axis (a) and long axis (b) of the cancer were measured with vernier calipers to calculate volume by using formula $V=ab^2$. The treatment with siRNA complex began, when the cancer volume was 70 $mm^3$. HA-PEI conjugate and siRNA were mixed in 5% glucose solution at a weight ratio of 1:3 to form a complex, and was injected into the cancer for 3 days to be a concentration of 3.5 µg siRNA. The cancer size was measured every 2 or 3 days for two weeks.

Figure 27:
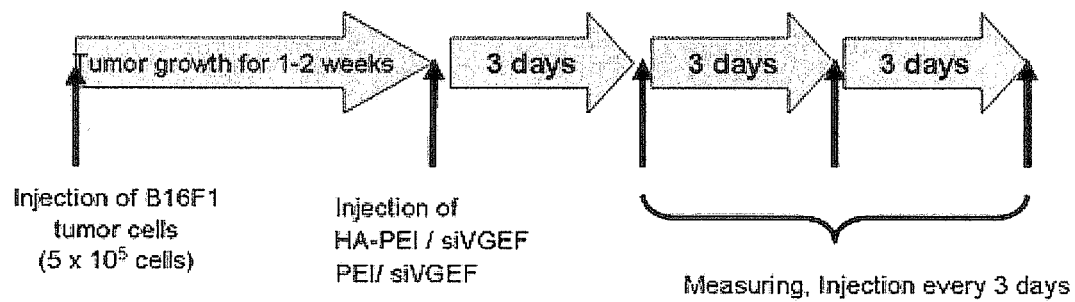
FIG. 27 is a schematic diagram of experiment testing the inhibition effect of VEGF-specific siRNA/HA-PEI complex on the size of cancer inoculated on mouse.
Figure 27:
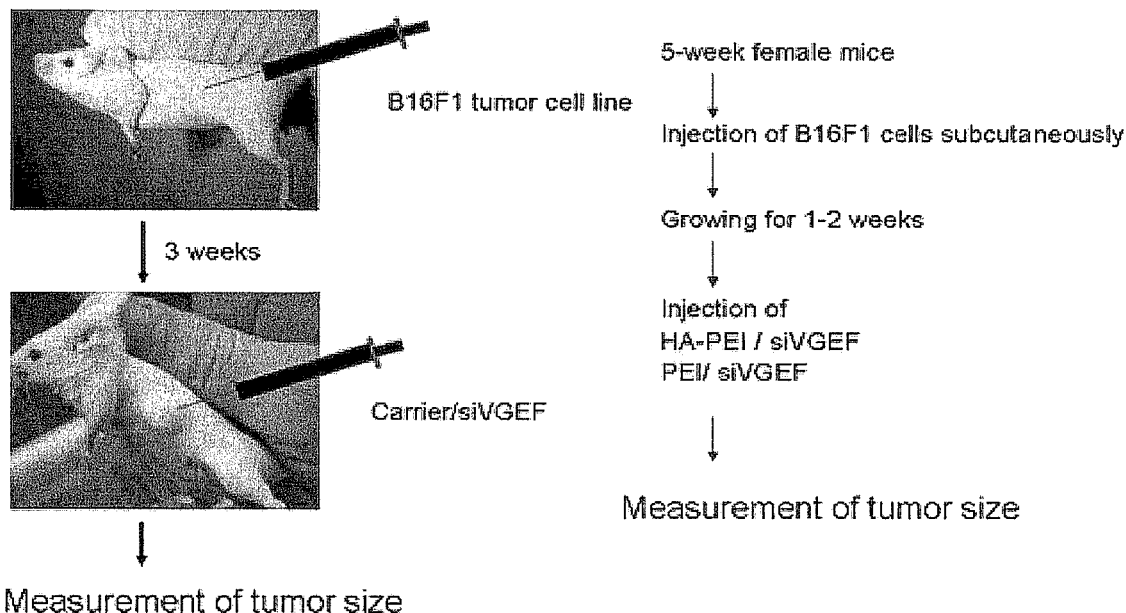
Figure 28:
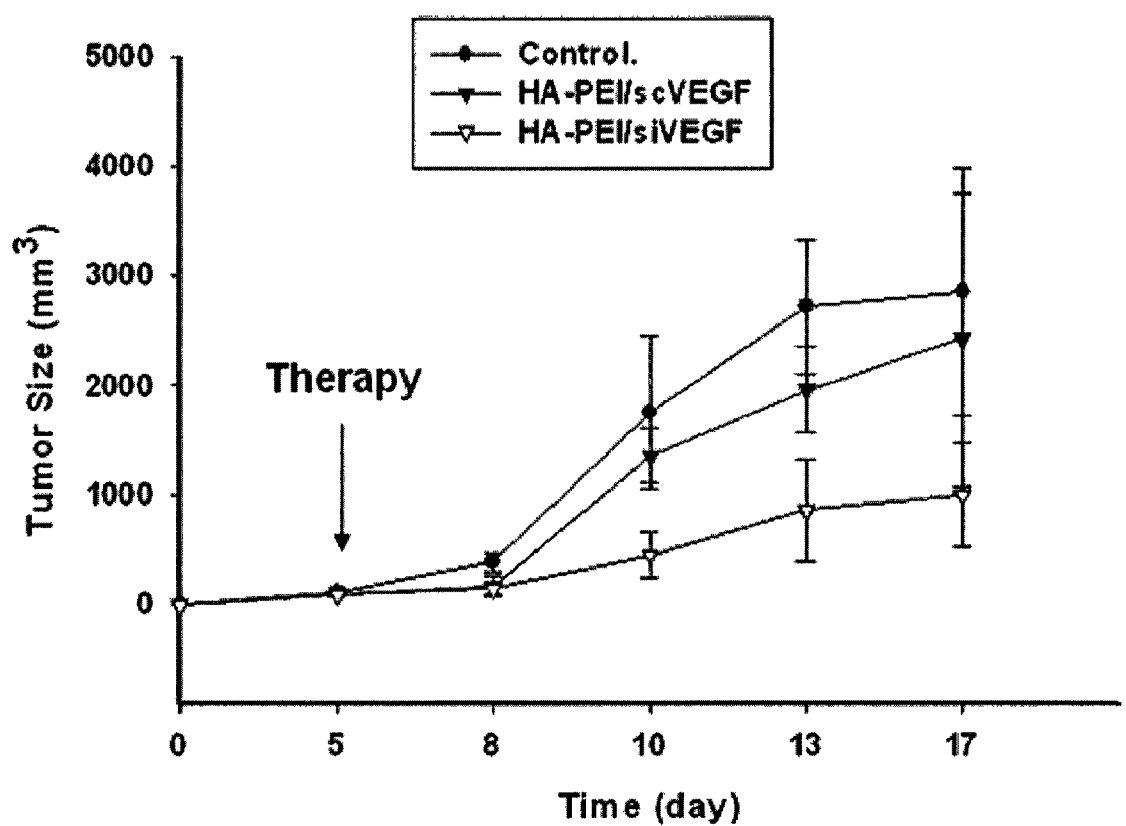
FIG. 28 shows a change in the size of cancer after administering siRNA/HA-PEI to mouse, no treatment group and a group administered by a complex including VEGF-nonspecific siRNA (scVEGF) and HA-PEI as control group. Compared with the control group, the complex of VEGF-specific siRNA (siVEGF) and HA-PEI reduced the growth of cancer significantly.

FIG. 27 is a schematic diagram of experiment testing the inhibition effect of VEGF-specific siRNA/HA-PEI complex on the size of cancer inoculated on mouse. As shown in FIG. 28, the HA-PEI/VEGF specific siRNA complex had anti-cancer activity compared to that of control group. FIG. 28 shows a change in the size of cancer after administering siRNA/HA-PEI to mouse, no treatment group and a group administered by a complex including VEGF-nonspecific siRNA (scVEGF) and HA-PEI as control group. Compared with the control groups, the complex of VEGF-specific siRNA (siVEGF) and HA-PEI reduced the growth of cancer significantly.

What is claimed is:

1. A composition for delivering a nucleic acid with 5 to 200 base pair length into a mammalian cell which comprises a cationic polymer conjugate obtained by conjugating polyethyleneimine and hyaluronic acid,
   wherein the hyaluronic acid has a molecular weight of 10 kD to 900 kD.

2. The composition of claim 1, wherein the polyethyleneimine has a molecular weight of 1 kD to 80 kD.

3. The composition of claim 1, wherein the hyaluronic acid is bonded with a compound having two or more carboxyl groups.

4. The composition of claim 3, wherein the compound having two or more carboxyl groups is glutamic acid, gamma-carboxyl glutamic acid, aspartic acid, or glutathione.

5. A composition for delivering a nucleic acid into a mammalian cell, comprising a complex containing a cationic polymer conjugate obtained by conjugating polyethyleneimine and hyaluronic acid, and a nucleic acid with 5 to 200 base pairs length through electrostatic binding,
   wherein the hyaluronic acid has a molecular weight of 10 kD to 900 kD.

6. The composition of claim 5, wherein the nucleic acid is a small interfering RNA (siRNA).

7. The composition of claim 5, wherein the nucleic acid is an antisense nucleic acid.

8. The composition of claim 5, wherein the cationic polymer conjugate and the nucleic acid is present in a weight ratio of 1:0.01 to 1:100.

* * * * *